(12) United States Patent
Medina-Bolivar et al.

(10) Patent No.: US 7,666,677 B2
(45) Date of Patent: Feb. 23, 2010

(54) PRODUCTION OF STILBENES IN PLANT HAIRY ROOT CULTURES

(76) Inventors: Luis Fabricio Medina-Bolivar, 112 Island Crest Cir., Memphis, TN (US) 38103; Maureen Dolan, 3701 Marchbanks Cir., Jonesboro, AR (US) 72401; Selester Bennett, 106 Lucas Drives No. 4, Blacksburg, VA (US) 24060; Jose M. Condori, 3700 S. Caraway Rd., Apt. K-1, Jonesboro, AR (US) 72404; John F. Hubstenberger, 823 Park Ave., Jonesboro, AR (US) 72401

( * ) Notice: Subject to any disclaimer, the term of this patent is extended or adjusted under 35 U.S.C. 154(b) by 4 days.

(21) Appl. No.: 11/773,178

(22) Filed: Jul. 3, 2007

(65) Prior Publication Data

US 2008/0032372 A1 Feb. 7, 2008

Related U.S. Application Data

(60) Provisional application No. 60/818,599, filed on Jul. 5, 2006.

(51) Int. Cl.
*C12N 15/82* (2006.01)
*C12N 15/83* (2006.01)
*A01H 5/06* (2006.01)

(52) U.S. Cl. .................. 435/469; 435/419; 435/468; 800/294

(58) Field of Classification Search ........................ None
See application file for complete search history.

(56) References Cited

U.S. PATENT DOCUMENTS

| | | | |
|---|---|---|---|
| 4,588,693 | A | 5/1986 | Strobel |
| 4,871,574 | A | 10/1989 | Yamazaki et al. |
| 6,451,590 | B1 | 9/2002 | Adelberg et al. |
| 6,753,178 | B2 | 6/2004 | Adelberg et al. |
| 6,974,895 | B1 | 12/2005 | Paiva et al. |
| 2002/0132021 | A1 | 9/2002 | Raskin |
| 2004/0111769 | A1 | 6/2004 | Chia et al. |

FOREIGN PATENT DOCUMENTS

WO WO03062406 A1 7/2003

OTHER PUBLICATIONS

Hain R. et al. Plant Molecular Biology 1990; vol. 15, pp. 325-335.*
Guillon S. et al. Current Opinion in Plant Biology 2006; vol. 9, pp. 341-346.*
Komarnytsky S. et al. Plant Cell Reports, 2004; vol. 22, pp. 765-773.*
Guillon et al. (2006) "Hairy root research: recent scenario and exciting prospects" Current Opinion in Plant Biology, 9:1-6.
Medina-Bolivar et al. (2004) "Production of recombinant proteins in hairy roots cultured in plastic sleeve bioreactors" Methods in Molecular Biology 267:351-363.
Medina-Bolivar and Olazabal, (Jun. 3, 2006) "Production of secondary metabolites and recombinant proteins in hairy roots cultured in the Liquid Lab (TM) bioreactor" Poster at In vitro Biology Meeting, Minneapolis, Minnesota.
Medina-Bolivar et al. (2007) "Production and secretion of resveratrol in hairy root cultures of peanut" Phytochemistry68:1992-2003.
GenBank accession No. DQ782955 Agrobacterium rhizogenes strain ATCC 15384 plasmid pRi 15834 3-indoleacetamide hydrolase (aux2) and tryptophan 2-monooxygenase (aux 1) genes, complete cds (available Jun. 21, 2006).
Davis et al. (1986) "Several biotic and abiotic elicitors act synergistically the induction of phytoalexin accumulation in soybean" Plant Molecular Biology, 6:23-32.
Chen et al. (2002) "Peanut roots as a source of resveratrol" J. Agric Food Chem. 50:1665-1667.
Huang et al. (2005) "Resveratrol derivatives from the roots of Vitis thunbergii" J. Nat. Prod. 68:217-220.
White, F. F et al.,(1985) J. Bacteriol., vol. 164, p. 33.
Hain et al. (1990) "Expression of a stilbene synthase gene in Nicotiana tabacum results in synthesis of the phytoalexin resveratrol" Plant Molecular Biology 15:325-335.
Presentation, Nov. 2006, UAMS, Aging Group—Medina-Bolivar/Dolan presentation.
Yu et al. Apr. 2006, "Contents comparison of resveratrol and polydatin in the wild Polygonum cuspidatum plant and its tissue cultures" Zhongguo Zhong yao za zhi ,College of Pharmacy, Hebei Medical University, Shijiazhuang, China 31 (8):637-41 (English abstract only) PMID: 16830819.
Hain et al. (19993) Nature, vol. 361: 153-156.
Komarnytsky et al. (20004) Plant Cell Reports, vol. 22: 765-773.
Tassoni et al. "Jasmonate and Na-orthovanadate promote resveratrol production in Vitis vinifera cv. Barbera cell cultures" new Phytologist (2005).
Bais et al. "Influence of exogenous hormones on growth and secondary metabolite production in hairy root cultures of Cichorium intybus L. cv. Lucknow Local" In Vitro Cellulase and Developmental Biology—Plant 37 (2) pp. 293-200 ISSN 1054-5476 (2001).

* cited by examiner

*Primary Examiner*—Russell Kallis
(74) *Attorney, Agent, or Firm*—Patricia A. Sweeney

(57) ABSTRACT

Improved methods for production of stilbenoids including resveratrol, pinosylvin and their respective derivatives are provided, including producing hairy roots from plant cells and eliciting production of the stilbenes. The plant cells in an embodiment are infected by *Agrobacterium* to produce hairy roots, and contacted with substances which elicit production of the stilbenoid compounds.

23 Claims, 16 Drawing Sheets trans-Resveratrol cis-Resveratrol

Piceid (polydatin)

Pterostilbene

Piceatannol

Resveratrol trimethylether

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtgacaagc agcgatgagc                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gattgcaaac ttgcactcgc                                                 20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaagcttgt cagaaaactt caggg                                           25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

-continued

```
ccggatccaa tacccagcgc ttt                                              23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgcccgatc gagctcaagt                                                  20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgacccaa acatctcggc t                                                21

<210> SEQ ID NO 7
<211> LENGTH: 4586
<212> TYPE: DNA
<213> ORGANISM: Agrobacterium rhizogenes

<400> SEQUENCE: 7
ggtaccaaag ttgtccaaga cgaatcccag tgtcctatta ccaatagccg gcgctagttt      60
gatttcagaa taaagagaaa ttcgtcacac caaatattag aagcaatgtt tgattgacca     120
tcatacttaa gatgaacatt ccaaacacag ttataatacg cattattatt gacacaatat     180
aaaattataa tgttgatatt ccttgaaata taatattaca atagataaag tagaggaaat     240
tatgtcagaa atttggtttg ctctgcttta cgacagagtc ggacgatgcc taaagtctat     300
tgcttcttct atcgctagtc caattgctaa cagacgttca tccgagcttg cagagccatc     360
gatttccatg ccaataggca gaccgttgga actaagagaa acgggaagac ttaggcccgg     420
caggcccgca ttactgctgg gatctacatt ccgcacgaag attttaaagg tatcggtcat     480
tgagccattg tgaatcaccg atagatcatg gccaattggc ttggctgtca acggagctgt     540
tgggaaaaga attgcatcta gctgatgcgc cttgaagtaa ctgtggtagg ccgcttggag     600
tctcggtctg aaaaaacgtc gcgccagaca atactcgctt ttggaaataa gattatccga     660
gagttgtgca ttgagaatac ttgcaacatc cggactgcga atcgctctga caacctcaga     720
aaaggaaaca ccctctacga agttctgaat ataatgttca agggacaacg gaaattcgta     780
gatggcagtc ggaaagctga cccccttcat gtgatgcgct aaatcaggaa tatctgcttc     840
aacaaaagta acatctttgc gtgccagaac tctgataatc gtctcggctg ctaaggcgac     900
atcgggctcc aggtcgttgt aaaagtaagc ggttggcaag cctatacgca gcccttcag      960 gcggaccgtt tgattaaccg gcggtctccc gcaaatgata ccgtcaagaa gaatcacgtc    1020
cggaacattc tgtgcgataa cgccaggggt gtcccgggtg gggcttaccg gaactattcc    1080
gtccgttgga tatcgcccca cggtaggacg aaacccacc acgccgcaca aggcggccgg     1140
taaacggacc gacgctcccg tgtcagttcc gacgccgccc agcatcaatc ggccggccac    1200
cgcggcggcc acacccccac ttgatccccc tgggatgaga ctagggttcc acgggtttcg    1260
tacggcgcct gtggcggagt tgttgctcgt gatcccaaaa gacaattcgt gcatgtttcc    1320
```

-continued

```
cgaagcgcca ggcagtgccc cagccgcgag aagttgtcgt gcaactccgg caggcgtctt    1380
gggtttgtgg ttctgtaagc ctggcgtacc agcggtcgcg gcgaacctgc ctgtcgcaat    1440
attcgcttta aagcataggg gaacgccagc taggccaaca ccggcacctc cgtgttgatc    1500
gattttgctg gcagtccacc gtaggtgcgc ccagtcggtt tccagaaagg cgtttaagga    1560
tcttgctgct tcacagcggg ctattatcgt ttcgattaac tcaaagcacg agtattttct    1620
ttccctgaga catttaagcg tctcggtgat cgaggagagg gtcaccattt tcgttgtgct    1680
gagggaactg agatagatct cgccagagaa acgttcaatg attttttgctt ggagtgaaaa    1740
aggcaaataa ttatagagga aggaagtcag aaatggctgc gcagtagggc cacttgtata    1800
agtgccggtc gaacactgct ggtggaaagt caaaagcgtg aagtattagt tgaactctgt    1860
tactaaattg agataaatgg gatatttttat tcgaaagtac tgtttgagat ctagcgacaa    1920
taataatgtc atcttatgag attgcatggc aatatggatc taatatttgg cataaataga    1980
tggtggtttt gtctccactt ttaaaccttc acagcgttac cctaacacct cttaattgcg    2040
tacactcctt tcaaccgcat caatggctgg atcctcctc acattgccat caactggctc    2100
agcgccccctt gatatgatgc ttatcgatga ttcagatctg ctgcaattgg gtctccagca    2160
ggtattctcg aagcggtaca cagagacacc gcagtcacgc tacaaactga ccaggagggc    2220
ttctccagac gtctcatctg gcgaaggcaa tgtgcatgcc cttgcgttca tatatgtcaa    2280
cgctgagacg ttgcagatga tcaaaaacgc tcgatcgcta accgaagcga acggcgtcaa    2340
agatcttgtc gccatcgacg ttccgccatt tcgaaacgac ttctcaagag cgctactcct    2400
tcaagtgatc aacttgttgg gaaacaaccg aaatgccgat gacgatctta gtcacttcat    2460
agcagttgct ctcccaaaca cgcccgctc taagatccta accacggcac cgttcgaagg    2520
aagcttgtca gaaaacttca gggggttccc gatcactcgt gaaggaaatg tggcatgtga    2580
agtgctagcc tatgggaata acttgatgcc caaggcctgc tccgattcct ttccaaccgt    2640
ggatcttctt tatgactatg gcaagttctt cgagagttgc gcggccgatg acgtatcgg    2700
ttatttttcct gaaggcgtta gcaaacctaa agtggctata attggcgcag gcatttccgg    2760
gctcgttgca gcgagcgaac tacttcatgc aggggtagac gatgttacgg tgtatgaggc    2820
gagtgatcgg cttggaggaa agctatggtc acacggattt aagagtgctc caaatgtgat    2880
agccgagatg ggggccatgc gttttccgcg aagtgaatca tgcttgttct tctatctcaa    2940
aaagcacgga ctggactccg ttggtctgtt cccgaatccg ggaagtgtcg ataccgcatt    3000
gttctacagg ggccgtcaat atatctggaa agcgggagag gagccaccgg agctgtttcg    3060
tcgtgtgcac catggatggc gcgcattttt gcaagatggc tatctccatg atggagtcat    3120
gttggcgtca ccgttagcaa ttgttgacgc cttgaagtta gggcatctac agcaggcgca    3180
tggcttctgg caatcttggc tcacatattt tgagcgagag tctttctctt ctggcatcga    3240
aaaaatgttc ttgggcaatc atcctccggg gggtgaacaa tggaattccc tagatgactt    3300
ggatctttc aaagcgctgg gtattggatc cggcggattc ggccctgtat ttgaaagtgg    3360
gtttatcgag atccttcgct tagtcgtcaa cgggtatgag gataacgtgc ggctgagtta    3420
cgaaggaatt tctgagctgc ctcataggat cgcctcacag gtaattaacg gcagatctat    3480
tcgcgagcgt acaattcacg ttcaagtcga gcagattgat agagaggagg ataaaataaa    3540
tatcaagatc aaaggaggaa aggttgaggt ctatgatcga gtactggtta catccgggtt    3600
tgcgaacatc gaaatgcgcc atctcctgac atcaagcaac gcattcttcc atgcagatgt    3660
```

-continued

```
aagccatgca ataggggaaca gtcatatgac tggtgcgtca aaactgttct tgctgactaa    3720
cgaaaaattc tggctacaac atcatttgcc atcgtgcata ctcaccaccg gcgttgcaaa    3780
ggcagtttat tgcttagact atgatccgcg agatccaagc ggcaaaggac tggtgttgat    3840
aagctatact tgggaggatg actcacataa gctcctagcc gtccccgaca aaagagaaag    3900
gttcgcatcg ctgcagcgcg atattgggag ggcattccca gattttgcca agcacctaac    3960
tcctgcagac gggaactatg atgataatat cgttcaacat gattggctga ctgatcccca    4020
cgctggcgga gcgtttaaac tgaaccgcag aggcaacgac gtatattcag aaaggctttt    4080
ctttcagccc tttgacgtaa tgcatcccgc ggacgtaaag ggactttact tggccggttg    4140
tagctgttcc ttcaccggag ggtgggttga tggtgccatt cagaccgcat gcaacgctac    4200
gtgtgcgatc atttatggtt cgggaggaac cctcaaagaa ggtaatccac tggcgcacgc    4260
ttggaagcgg tataggtatc aagcgtgata atgcaacagt tagaataatt agtttgccct    4320
agccggtatt ccttggtgtt ccaatagggt tccgaagcca ataggcgaaa aagctgactt    4380
ttcagtccct tttattattc aattcgcttc ggtccaagca taattgtaac gctacgtgat    4440
agaaaaatgg aaattgacag attacttact taaattaata taatctatta atatcgtcaa    4500
gctaaaaaca tgtaatacgt aaatatatgg aaactttatg tctgaaaaga ccacattatt    4560
attgatcgta atacactgaa tctaga                                         4586
```

<210> SEQ ID NO 8
<211> LENGTH: 465
<212> TYPE: PRT
<213> ORGANISM: Agrobacterium rhizogenes

<400> SEQUENCE: 8

```
Val Thr Leu Ser Ser Ile Thr Glu Thr Leu Lys Cys Leu Arg Glu Arg
 1               5                  10                  15

Lys Tyr Ser Cys Phe Glu Leu Ile Glu Thr Ile Ile Ala Arg Cys Glu
            20                  25                  30

Ala Ala Arg Ser Leu Asn Ala Phe Leu Glu Thr Asp Trp Ala His Leu
        35                  40                  45

Arg Trp Thr Ala Ser Lys Ile Asp Gln His Gly Gly Ala Gly Val Gly
    50                  55                  60

Leu Ala Gly Val Pro Leu Cys Phe Lys Ala Asn Ile Ala Thr Gly Arg
65                  70                  75                  80

Phe Ala Ala Thr Ala Gly Thr Pro Gly Leu Gln Asn His Lys Pro Lys
                85                  90                  95

Thr Pro Ala Gly Val Ala Arg Gln Leu Leu Ala Ala Gly Ala Leu Pro
            100                 105                 110

Gly Ala Ser Gly Asn Met His Glu Leu Ser Phe Gly Ile Thr Ser Asn
        115                 120                 125

Asn Ser Ala Thr Gly Ala Val Arg Asn Pro Trp Asn Pro Ser Leu Ile
    130                 135                 140

Pro Gly Gly Ser Ser Gly Gly Val Ala Ala Val Ala Gly Arg Leu
145                 150                 155                 160

Met Leu Gly Gly Val Gly Thr Asp Thr Gly Ala Ser Val Arg Leu Pro
                165                 170                 175

Ala Ala Leu Cys Gly Val Val Gly Phe Arg Pro Thr Val Gly Arg Tyr
            180                 185                 190

Pro Thr Asp Gly Ile Val Pro Val Ser Pro Thr Arg Asp Thr Pro Gly
        195                 200                 205
```

-continued

```
Val Ile Ala Gln Asn Val Pro Asp Val Ile Leu Leu Asp Gly Ile Ile
    210                 215                 220

Cys Gly Arg Pro Pro Val Asn Gln Thr Val Arg Leu Lys Gly Leu Arg
225                 230                 235                 240

Ile Gly Leu Pro Thr Ala Tyr Phe Tyr Asn Asp Leu Glu Pro Asp Val
                245                 250                 255

Ala Leu Ala Ala Glu Thr Ile Ile Arg Val Leu Ala Arg Lys Asp Val
            260                 265                 270

Thr Phe Val Glu Ala Asp Ile Pro Asp Leu Ala His His Asn Glu Gly
        275                 280                 285

Val Ser Phe Pro Thr Ala Ile Tyr Glu Phe Pro Leu Ser Leu Glu His
    290                 295                 300

Tyr Ile Gln Asn Phe Val Glu Gly Val Ser Phe Ser Glu Val Val Arg
305                 310                 315                 320

Ala Ile Arg Ser Pro Asp Val Ala Ser Ile Leu Asn Ala Gln Leu Ser
                325                 330                 335

Asp Asn Leu Ile Ser Lys Ser Glu Tyr Cys Leu Ala Arg Arg Phe Phe
            340                 345                 350

Arg Pro Arg Leu Gln Ala Ala Tyr His Ser Tyr Phe Lys Ala His Gln
        355                 360                 365

Leu Asp Ala Ile Leu Phe Pro Thr Ala Pro Leu Thr Ala Lys Pro Ile
    370                 375                 380

Gly His Asp Leu Ser Val Ile His Asn Gly Ser Met Thr Asp Thr Phe
385                 390                 395                 400

Lys Ile Phe Val Arg Asn Val Asp Pro Ser Ser Asn Ala Gly Leu Pro
                405                 410                 415

Gly Leu Ser Leu Pro Val Ser Leu Ser Ser Asn Gly Leu Pro Ile Gly
            420                 425                 430

Met Glu Ile Asp Gly Ser Ala Ser Ser Asp Glu Arg Leu Leu Ala Ile
        435                 440                 445

Gly Leu Ala Ile Glu Glu Ala Ile Asp Phe Arg His Arg Pro Thr Leu
    450                 455                 460

Ser
465

<210> SEQ ID NO 9
<211> LENGTH: 740
<212> TYPE: PRT
<213> ORGANISM: Agrobacterium rhizogenes

<400> SEQUENCE: 9

Ala Gly Ser Ser Phe Thr Leu Pro Ser Thr Gly Ser Ala Pro Leu Asp
1               5                   10                  15

Met Met Leu Ile Asp Asp Ser Asp Leu Leu Gln Leu Gly Leu Gln Gln
            20                  25                  30

Val Phe Ser Lys Arg Tyr Thr Glu Thr Pro Gln Ser Arg Tyr Lys Leu
        35                  40                  45

Thr Arg Arg Ala Ser Pro Asp Val Ser Ser Gly Glu Gly Asn Val His
    50                  55                  60

Ala Leu Ala Phe Ile Tyr Val Asn Ala Glu Thr Leu Gln Met Ile Lys
65                  70                  75                  80

Asn Ala Arg Ser Leu Thr Glu Ala Asn Gly Val Lys Asp Leu Val Ala
                85                  90                  95

Ile Asp Val Pro Pro Phe Arg Asn Asp Phe Ser Arg Ala Leu Leu Leu
            100                 105                 110
```

```
Gln Val Ile Asn Leu Leu Gly Asn Asn Arg Asn Ala Asp Asp Leu
            115                 120                 125

Ser His Phe Ile Ala Val Ala Leu Pro Asn Ser Ala Arg Ser Lys Ile
        130                 135                 140

Leu Thr Thr Ala Pro Phe Glu Gly Ser Leu Ser Glu Asn Phe Arg Gly
145                 150                 155                 160

Phe Pro Ile Thr Arg Glu Gly Asn Val Ala Cys Glu Val Leu Ala Tyr
                165                 170                 175

Gly Asn Asn Leu Met Pro Lys Ala Cys Ser Asp Ser Phe Pro Thr Val
            180                 185                 190

Asp Leu Leu Tyr Asp Tyr Gly Lys Phe Phe Glu Ser Cys Ala Ala Asp
        195                 200                 205

Gly Arg Ile Gly Tyr Phe Pro Glu Gly Val Ser Lys Pro Lys Val Ala
210                 215                 220

Ile Ile Gly Ala Gly Ile Ser Gly Leu Val Ala Ala Ser Glu Leu Leu
225                 230                 235                 240

His Ala Gly Val Asp Asp Val Thr Val Tyr Glu Ala Ser Asp Arg Leu
                245                 250                 255

Gly Gly Lys Leu Trp Ser His Gly Phe Lys Ser Ala Pro Asn Val Ile
            260                 265                 270

Ala Glu Met Gly Ala Met Arg Phe Pro Arg Ser Glu Ser Cys Leu Phe
        275                 280                 285

Phe Tyr Leu Lys Lys His Gly Leu Asp Ser Val Gly Leu Phe Pro Asn
290                 295                 300

Pro Gly Ser Val Asp Thr Ala Leu Phe Tyr Arg Gly Arg Gln Tyr Ile
305                 310                 315                 320

Trp Lys Ala Gly Glu Glu Pro Pro Glu Leu Phe Arg Arg Val His His
                325                 330                 335

Gly Trp Arg Ala Phe Leu Gln Asp Gly Tyr Leu His Asp Gly Val Met
            340                 345                 350

Leu Ala Ser Pro Leu Ala Ile Val Asp Ala Leu Lys Leu Gly His Leu
        355                 360                 365

Gln Gln Ala His Gly Phe Trp Gln Ser Trp Leu Thr Tyr Phe Glu Arg
370                 375                 380

Glu Ser Phe Ser Ser Gly Ile Glu Lys Met Phe Leu Gly Asn His Pro
385                 390                 395                 400

Pro Gly Gly Glu Gln Trp Asn Ser Leu Asp Asp Leu Asp Leu Phe Lys
                405                 410                 415

Ala Leu Gly Ile Gly Ser Gly Phe Gly Pro Val Phe Glu Ser Gly
            420                 425                 430

Phe Ile Glu Ile Leu Arg Leu Val Val Asn Gly Tyr Glu Asp Asn Val
        435                 440                 445

Arg Leu Ser Tyr Glu Gly Ile Ser Glu Leu Pro His Arg Ile Ala Ser
450                 455                 460

Gln Val Ile Asn Gly Arg Ser Ile Arg Glu Arg Thr Ile His Val Gln
465                 470                 475                 480

Val Glu Gln Ile Asp Arg Glu Asp Lys Ile Asn Ile Lys Ile Lys
                485                 490                 495

Gly Gly Lys Val Glu Val Tyr Asp Arg Val Leu Val Thr Ser Gly Phe
            500                 505                 510

Ala Asn Ile Glu Met Arg His Leu Leu Thr Ser Ser Asn Ala Phe Phe
        515                 520                 525
```

-continued

```
His Ala Asp Val Ser His Ala Ile Gly Asn Ser His Met Thr Gly Ala
    530                 535                 540

Ser Lys Leu Phe Leu Leu Thr Asn Glu Lys Phe Trp Leu Gln His His
545                 550                 555                 560

Leu Pro Ser Cys Ile Leu Thr Thr Gly Val Ala Lys Ala Val Tyr Cys
                565                 570                 575

Leu Asp Tyr Asp Pro Arg Asp Pro Ser Gly Lys Gly Leu Val Leu Ile
            580                 585                 590

Ser Tyr Thr Trp Glu Asp Asp Ser His Lys Leu Leu Ala Val Pro Asp
        595                 600                 605

Lys Arg Glu Arg Phe Ala Ser Leu Gln Arg Asp Ile Gly Arg Ala Phe
    610                 615                 620

Pro Asp Phe Ala Lys His Leu Thr Pro Ala Asp Gly Asn Tyr Asp Asp
625                 630                 635                 640

Asn Ile Val Gln His Asp Trp Leu Thr Asp Pro His Ala Gly Gly Ala
                645                 650                 655

Phe Lys Leu Asn Arg Arg Gly Asn Asp Val Tyr Ser Glu Arg Leu Phe
            660                 665                 670

Phe Gln Pro Phe Asp Val Met His Pro Ala Asp Lys Gly Leu Tyr
        675                 680                 685

Leu Ala Gly Cys Ser Cys Ser Phe Thr Gly Gly Trp Val Asp Gly Ala
    690                 695                 700

Ile Gln Thr Ala Cys Asn Ala Thr Cys Ala Ile Ile Tyr Gly Ser Gly
705                 710                 715                 720

Gly Thr Leu Lys Glu Gly Asn Pro Leu Ala His Ala Trp Lys Arg Tyr
                725                 730                 735

Arg Tyr Gln Ala
            740
```

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccggtaccaa agttgtccaa gacgaatccc ag            32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaagcttgg tgaccctctc ctcgatcacc              30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

-continued

```
ccggtaccaa agttgtccaa gacgaatccc a                                    31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgaattcgg atccagccat tgatgcggtt                                      30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccggtaccgg tcaccatttt cgttgtgctg                                      30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgaattcca ttgttcaccc cccg                                            24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgaattccc tagatgactt ggat                                            24

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctctagatt cagtgtatta cgatcaataa                                      30
```

PRODUCTION OF STILBENES IN PLANT HAIRY ROOT CULTURES

REFERENCE TO RELATED APPLICATIONS

This application in a continuation-in-part and claims priority to previously filed application U.S. Ser. No. 60/818,599 filed Jul. 5, 2006, the contents of which are incorporated in their entirety.

BACKGROUND

Trans-resveratrol (trans-3,4',5-trihydroxystilbene, FIG. 1), and derivatives such as piceid (Larronde et al., 2005; Rimando and Barney, 2005), along with pinosylvin (Celimene et al., 1999) belong to a class of naturally occurring defense compounds that are produced in a select number of plant species and known as stilbenes. These plant polyphenols are receiving considerable interest based upon a number of associated health benefits (Baur and Sinclair, 2006; Delmas et al., 2006). Most notably, the significant levels of the resveratrol metabolite in red wine have been credited to the phenomenon referred to as "the French Paradox". It was observed in a large population study that prolonged, moderate consumption of red wine correlated with a very low incidence of cardiovascular disease (most notably coronary heart disease) among this study group despite a life-style that included a high saturated fat diet, little exercise and widespread smoking (Frankel et al., 1993; Kopp, 1998). Over the last decade, resveratrol has been reported to be associated with numerous other health benefits ranging from its function as a general anti-oxidant, to its anti-cancer, -atherosclerosis and -aging properties and most recently its neuroprotective and estrogenic activities (Gehm et al., 1997; Miura et al. 2003; Orallo, 2006). Furthermore several natural derivatives of resveratrol have shown additional health benefits including a methylated resveratrol compound, pterostilbene (FIG. 1), that has been shown to reduce cholesterol levels in laboratory animals (Rimando et al., 2005). Pinosylvin, another relative in the stilbene pathway has been associated with anti-inflammatory and cancer chemopreventative activities (Park et al., 2004).

With a growing trend in the United States and the continued popularity in Europe and Asia, for seeking natural health enhancing products, many plant-derived nutraceuticals are being incorporated into the functional food industry, the herbal and dietary supplement markets, and pharmaceutical industry. Countless studies have shown that US consumers often prefer foods with added health benefits over the same food without the benefit, and inclusion of these health-enhancing compounds in food products is preferred to taking dietary supplements. While dried or extracted plant material (seeds, roots, rhizomes, etc.) enriched in resveratrol and other stilbenes are incorporated into a number of marketed products that include dietary supplements (i.e. Longevinex™) and health-enhancing food products (i.e. Old Orchard Beverage Company, Sparta, Mich.), this source of resveratrol and other stilbenes is typically associated with color pigments and numerous other components that limit their broader application into food, nutritional and cosmetic products. A high quality source of naturally-derived resveratrol and its many derivatives that is void of color, taste, odor as well as production contaminants (i.e. pesticide residues, heavy metals, etc.) is currently not available on the commercial market due to a lack of consistent, high volume, cost-effective production systems for these health beneficial plant metabolites.

Efforts to advance production systems for providing more enriched and concentrated commercial stocks of resveratrol have taken several distinct strategies. The reconstruction of a biochemical pathway in a heterologous host to produce resveratrol was first demonstrated in wine yeasts with the intent of increasing resveratrol production for health benefits during fermentation in both red and white wines (Becker et al., 2003). More recent efforts have successfully co-expressed several genes belonging to the stilbene biosynthesis pathway of peanut in $E.\ coli$ (Watts et al., 2006). While the conversion of the substrate 4-coumaric acid was functional in this recombinant microbial bioproduction system and produces over 50 times the levels of resveratrol than recombinant yeast (100 mg/L in $E.\ coli$), issues of inefficient substrate utilization, high substrate cost and recombinant-based production issues currently limit commercialization efforts of resveratrol product from these systems. In other attempts to produce resveratrol, genes encoding resveratrol were introduced into legume plant cells (Paiva et al., U.S. Pat. No. 6,974,895). Lengthy process steps and cost are among the disadvantages of such systems.

The use of a natural plant-based bioproduction approach for producing this plant-derived resveratrol has several advantages. While the use of grapevine cell suspensions for the production of trans-resveratrol has reported levels as high as 15 mM in the spent medium (Bru et al., 2006), there are issues surrounding long-term stability of plant cell cultures for secondary metabolite production (Wink et al., 2005). Such cultures are undifferentiated and in order to maintain the cultures ongoing hormone exposure is required, and stability becomes a problem. The culture can stop producing the stilbene and not respond to elicitors.

Accordingly, there exists a need to improve on systems for controlled, contained production of enriched fractions of natural stilbenoids that include resveratrol, pinosylvin and their respective derivatives.

DESCRIPTION OF PREFERRED EMBODIMENTS

Figure 1:
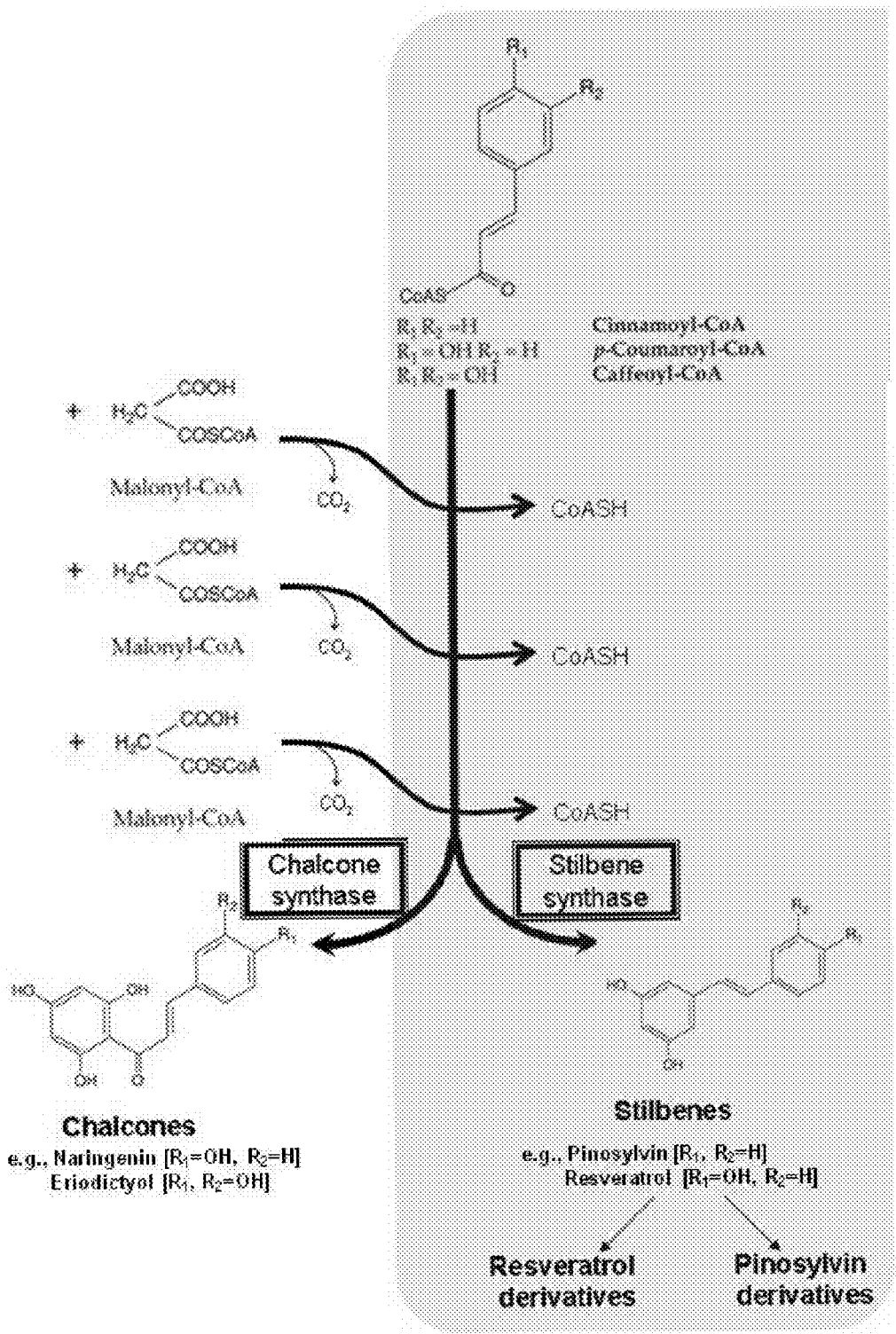
FIG. 1 shows the biosynthetic pathway of stilbenes, including resveratrol and derivatives and pinosylvin and derivatives.

Stilbenes, including resveratrol and pinosylvin, have garnered much interest over the past few decades due to various health benefits associated with these plant secondary metabolites. Resveratrol is a popular, natural antioxidant molecule associated with cardiovascular and anticancer health benefits. Resveratrol exists as both the trans- and cis-isomer with numerous reports suggesting trans-resveratrol to be the most bioactive form of this molecule (Roupe et al., 2006a). Trans-resveratrol can readily be converted to cis-resveratrol when exposed to UV light and is unstable when exposed to high pH conditions. In addition to the resveratrol isomers, derivatives of resveratrol that include but are not limited to glucosylated, prenylated, methylated, hydoxylated modifications as well as tetramers of resveratrol have been linked with beneficial activities. Several of these forms of resveratrol may in fact provide enhanced bioavailability and performance profiles surpassing that observed for the free resveratrol isomers (Chang et al., 2006; Roupe et al., 2006b; Wenzel and Somoza, 2005; Soleas et al., 2001). Some examples include naturally occurring monomethylether analogues of resveratrol that may be important in the inhibition of CYP1A2 and CYP2E1's potential chemopreventive activity (Mikstacka et al., 2006). Several novel and previously identified resveratrol derivatives including several vitisinols, vineferal and ε-viniferin from the roots of *Vitis thunbergii* showed significant antioxidative and antiplatelet activities (Huang et al., 2005). Recent identification of a tetrameric form of resveratrol, vaticanol B, appears to have potent anti-inflammmatory properties in protecting cells against ER stress-induced cell death (Tabata et al., 2007). Arachidin-1 and -3 are prenylated derivatives of resveratrol found in peanuts and show favorable anti-inflammatory and antioxidant activities in a cell model (Chang et al., 2006). Likewise, pinosylvin and its derivatives have shown promise as anti-inflammatory and chemopreventative agents (Park et al., 2004; Lee et al., 2006). The above lists a few examples and many other derivatives are known or remained to be identified and included within the scope of the invention. While resveratrol, pinosylvin, and their respective derivatives can be recovered as an extract from a variety of plants, these products sourced from raw botanical material may not be suitable for all applications in the food/pharmaceutical sectors due to endogenous plant impurities/associated color (i.e. phenolic compounds, tannins, etc.) or production impurities (i.e. chemical residues, heavy metals, soil pathogens). In addition, these secondary metabolites are generally recovered from the raw botanical material at relatively low concentrations. Finally, stilbene yields can be highly variable from lot to lot of this raw botanical material due to the impact of environmental factors in the field.

The inventors have shown that plant hairy roots, produced via infection with *Agrobacterium*, offer a novel and sustainable plant tissue-based system for the bioproduction of valued secondary metabolites including the stilbenoids resveratrol, pinosylvin and their respective derivatives. These roots reflect the metabolic phenotype of the host plant, yet are unique in their genetic and biosynthetic stability, providing advantages in production sustainability when compared with plant cell culture systems. Recent progress in the scale-up of hairy root cultures, such as the use of a low cost mist bioreactor for commercial production of the anticancer camptothecin, continues to advance this system as an attractive tool for industrial processes (Wink et al., 2005; Guillon et al., 2006). Further, production of increased amounts of the trans-isomer of resveratrol as well as other valued stilbene derivatives in medium and root has been demonstrated through hairy root elicitation of this plant tissue culture platform.

Figure 2:
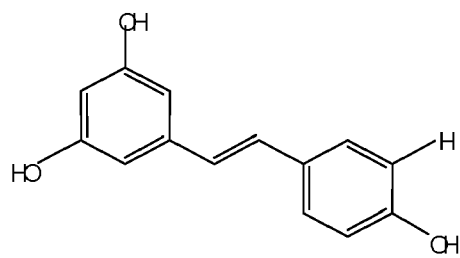
FIG. 2 is a diagram in which the chemical structures of resveratrol and select resveratrol derivatives are shown.
Figure 2:
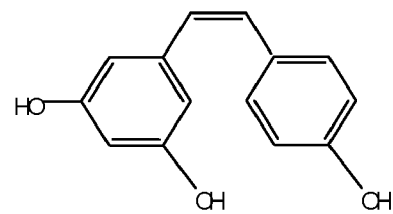
Figure 2:
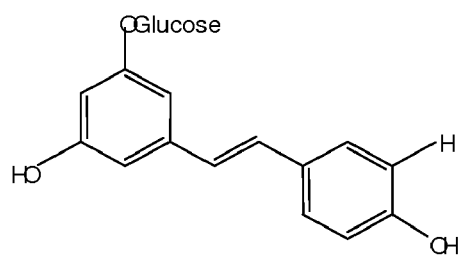
Figure 2:
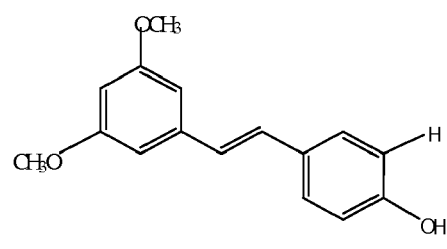
Figure 2:
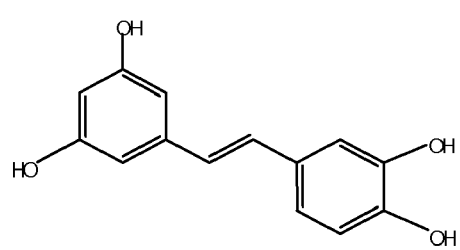
Figure 2:
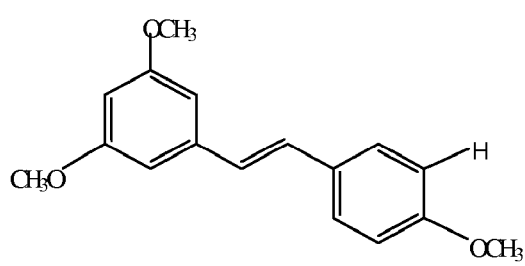

The following abbreviations are used here: B5, Gamborg's B5 medium with 2% sucrose (Gamborg et al., 1968); cv., cultivar; HPTLC, high performance thin layer chromatography; HPLC, high performance liquid chromatography; Rf, retardation factor; Rt, retention time; TLC, thin layer chromatography With establishment of hairy root cultures from a wide variety of selected plant species, the inventors have discovered that stilbenes, including resveratrol, pinosylvin and their respective derivatives can be produced without inclusion of a transgene encoding key enzymes (such as those encoding resveratrol synthase, the enzyme involved in the synthesis of resveratrol; Chun et al., 2001). These stilbenes have been reported to be produced naturally in a wide range of plant species (Aggarwal et al., 2004). What is more, hairy root cultures can also be used with plants transformed with genes encoding a stilbene synthase enzyme. Stilbenes are naturally occurring defense compounds derived from the activity of a stilbene synthase (i.e. resveratrol synthase or pinosylvin synthase). A stilbene synthase enzyme defines an important regulatory entry point to the stilbene biosynthetic pathway as shown in FIG. 1. By use of the term stilbene or stilbene composition is meant: (i) resveratrol and/or all natural resveratrol derivatives, including, for example, those shown in FIG. 2 and any other identified as derivatives of resveratrol and (ii) pinosylvin and/or all natural pinosylvin derivatives. Since these stilbene derivatives are typically present and recoverable in only small amounts from field-grown raw botanical material, we believe the hairy root production platform may offer a viable, scaleable, production alternative for naturally sourced resveratrol, resveratrol derivatives and other valued stilbenes. When referring to a resveratrol composition is meant to include resveratrol, resveratrol derivatives or combinations of same. Likewise, when referring to a pinosylvin composition is meant pinosylvin, pinosylvin derivatives, and combinations of same.

Hairy root disease was first identified as a problem in select plants caused by *Agrobacterium rhizogenes*, which can be isolated from the soil. The gram-negative bacterium transfers DNA from its root-inducing (Ri) plasmid into the genome of the infected plant cell which results in the formation of roots. Its use in the control of beneficial growth of roots was described by Strobel, U.S. Pat. No. 4,588,693. (This reference and all references cited herein are incorporated herein by reference.) In the production of hairy root cultures, the plant is infected with the *Agrobacterium* by exposure of plant cells or plant parts to *Agrobacterium*. For example, The rol genes containing genes rolA, rolB and rolC (F. F. White et al., (1985)) are present in the T-DNA of *Agrobacterium rhizogenes* Ri plasmid and expression of these genes induce the formation of hairy roots. Any plant part, tissue or cell capable of producing hairy roots can be used in the invention. Such plant parts can include, for example and without limitation, plant stem, petiole, cotyledonary node, hypocotyl, or other plant parts or cells. A semi-solid medium or liquid nutrient solution is preferably employed which is optimized for maintenance of roots, resulting in increased growth rate of roots compared to non-infected plant cells. While many types of material and solutions and medium are known and can be used in the invention, several preferred examples include Murashige and Skoog and Gamborg B5 medium. Several media modifications optimized for meeting in vitro nutrient requirements of different host plants used in making sustainable hairy root cultures can be employed.

Further, the inventors have developed vectors for producing hairy roots in plants, which contain both the rol genes and aux genes in a single transfer DNA (T-DNA). This vector allows sustained growth of the hairy root line without the use of auxins since both rol and aux genes are inserted in the same plant cell DNA. Screening for several lines of hairy roots results in identification of a line that can sustain growth in liquid after several subculturing events on semi-solid medium. A vector with both rol and aux genes reduces the time in obtaining stable high growth/stilbene-secreting hairy roots. Such vectors can be used in *A. tumefaciens*, such as strains EHA105 and LBA4404 or *A. rhizogenes* strains such as R1000 and ATCC 15834.

The hairy roots are then exposed to an elicitory substance to produce the stilbenoid compounds including resveratrol, pinosylvin, and associated derivatives of these molecules. A vast number of elicitors are known to one skilled in the art, as set forth, for example, at Raskin, US publication no. 20020132021. Among elicitors known to be effective in eliciting resveratrol are the cyclodextrins, including randomly methylated β-cyclodextrin, cellulase, laminarin, chitosan, sodium acetate, copper sulfate, ultraviolet light, jasmonates, sodium orthovanadate (Rudolf and Resurreccion, 2005; Tassoni et al., 2005; Bru et al., 2006). While certain elicitors may produce optimum results, the person skilled in the art will appreciate that a number of different elicitors are available for use in the invention.

Resveratrol, pinosylvin, and derivatives may be obtained from the roots, medium or solution and extracted by known procedures, and the invention is not limited by any particular extraction procedure. For example, column chromatography, crystallization, distillation, liquid or solid phase extraction are among many techniques known in the art. An example of one such process is use of a solvent which can create two phases capable of separation, such as ethyl acetate. This provides advantages over use of solvents such as methanol, where drying is required because methanol and water are miscible and two phases are not produced. However, since the media used may be rich in sugars these can bind some of the stilbenoids, resveratrol and pinosylvin, causing a drastic decrease in recovery.

Assay and analysis of resveratrol may be conducted through any variety of methods, and can include, for example, taking advantage of natural fluorescence of the compound when exposed to ultraviolet light. Thin layer chromatography, high performance thin layer chromatography (Babu et al., 2005), high performance liquid chromatography, and gas chromatography-mass spectrometry are among the examples of assays that may be used to assay the resveratrol produced.

Reference to plants includes whole plants as well as plant cells and plant parts such as tissues, or protoplasts from the plant or organism, cell cultures, tissue cultures, calli, embryos, and seeds. Plants that are useful in the invention are those naturally producing resveratrol, which include *Pinus sibirica, Pinus sylvestris, Gnetum parviflorum, Vitis vinifera, Vitis rotundifolia, Polygonum cuspidatum, Arachis hypogaea, Eucaliptus* sp., *Artocarpus lakoocha, Nothofagus fusca, Phoenix dactilifera, Festuca versuta, Carex fedia, Veratrum grandiflorum, Cassia quinquangulata, Lycopersicon esculentum, Gossypium hirsutum* and any other plant species shown to produce resveratrol. In a preferred embodiment of the invention the plant is *Arachis hypogaea*. In another preferred embodiment the plant is *Vitis rotundifolia*. In another preferred embodiment the plant is *Polygonum cuspidatum*. In another preferred embodiment stilbenes are produced from non-transgenic *Nicotiana*, such as *Nicotiana benthamiana*.

In one embodiment of the invention, one may also employ in the process a plant which does not naturally produce stilbenes including resveratrol and pinosylvin, but which has been genetically engineered so that it produces stilbenes. As discussed herein, any plant that can be genetically engineered could be transformed with a nucleotide sequence expressing a stilbene synthase (i.e. resveratrol synthase or pinosylvin synthase). In an additional embodiment, a plant may be genetically engineered to co-express a stilbene synthase (i.e. resveratrol synthase or pinosylvin synthase) with one or more genes involved in the production of a resveratrol or pinosylvin derivative. For example, Hall and De Luca (2001) cloned a glucosyl transferase from Concord grape (*Vitis labrusca*) that can use resveratrol as substrate. In one example, co-expression of resveratrol synthase and this resveratrol glucosyl transferatese can lead to the production of resveratrol glucosides. Hall and De Luca also show that resveratrol glucosyl transferase can use different phenolic compounds as substrates. Because many of the enzymes catalyzing the downstream modifications of resveratrol or pinosylvin may also accept different phenolic compounds as substrates, one may predict that other enzymes that also use as substrates other phenolic compounds may also accept resveratrol or pinosylvin and produce resveratrol or pinosylvin derivatives. These enzymes are not limited to glucosyl transferases, prenyltransferases, methyltransferases and hydroxylases. Specific examples of these enzymes are flavonoid-O-methyltransferases, caffeoyl-CoA methyltransferase, cinnamoyl-CoA methyltransferase, geranyltransferase and any other enzyme that could accept a stilbenes compound as substrate. Using general plant transformation methods, genes encoding these enzymes could be co-expressed with a stilbene synthase or express in a transgenic plant already expressing a stilbene synthase. In addition, plants naturally producing stilbenes can be engineered with an enzyme to produce a specific class of derivative and hairy roots can be produced from these engineered plants.

Plants transformed with a gene encoding a stilbene synthase, for example resveratrol synthase or pinosylvin synthase, include any plant capable of being so transformed, including, without limitation, plants that may be used for food and feed, such as corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), potato (*Solanum tuberosum*); and peas (*Lathyrus* spp.). Alternatively, the transgenic plant may be a species that is not conventionally eaten, such as tobacco (*Nicotiana tabacum*), tea (*Camellia sinensis*), flax (*Linum*), sisal (*Agave sisalana*), firs, and cedars. Production of transgenic plants with a nucleotide sequence encoding resveratrol synthase is known, such as that discussed at Paiva et al., U.S. Pat. No. 6,974,895 and Chia et al. US publication no. 20040111760. The resulting transgenic plant or plant cell can then be induced to produce hairy roots using the process of the invention, and resveratrol or other stilbenoids could be recovered. Further, one appreciates that it falls within the scope of the invention to introduce into plant cells other desirable nucleotide sequences and then produce hairy roots from the plant cells, whether the plant naturally produces resveratrol, pinosylvin or related derivatives or is genetically engineered to produce these secondary metabolites.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989. *Molecular Cloning: A Laboratory Manual*, $2^{nd}$ Edition. Cold Spring Harbor Laboratory Press, Plainview, N.Y.).

A vector is typically prepared comprising the gene encoding a molecule, such as stilbene synthase, which produces stilbenoids, a promoter that will drive expression of the gene in the plant and a terminator region. In this regard, any plant-compatible promoter elements can be employed in the construct, influenced by the end result desired. Those can be plant gene promoters, such as, for example, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al., (1987) *Science* 236:1299 and European patent application No. 0 342 926; the barley lipid transfer protein promoter, LTP2 (Kalla et al., *Plant J.* (1994) 6(6): 849-60); the ubiquitin promoter (see for example U.S. Pat. No. 5,510,474); the END2 promoter (Linnestad et al. U.S. Pat. No. 6,903,205); and the polygalacturonase PG47 promoter (See Allen and Lonsdale, *Plant J.* (1993) 3:261-271; WO 94/01572; U.S. Pat. No. 5,412,085) and rice actin promoter (McElroy et al. (1990) *Plant Cell* 2:163-171). See international application WO 91/19806 for a review of various plant promoters also suitably employed in plant gene expression.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in connection with a gene expressing resveratrol or other stilbenoid molecules. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. A tissue specific promoter with preferential expression in hairy roots is preferred. Such a promoter is for example the Super P promoter which harbors elements from the mannopine synthase and octopine synthase genes. This promoter has been shown to have strong expression in hairy root and low in leaves (Nopo-Olazabal et al., 2005). There are a wide variety of other tissue-preferred promoters and, by way of example, include those described in Yamamoto et al. (1997) Plant J. 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505.

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette may also include at the 3' terminus of the heterologous nucleotide sequence, a transcriptional and translational termination region functional in plants. Convenient termination regions are available from the Ti-plasmid of *A. tumefaciens*, such as the octopine synthase and nopaline synthase (nos) termination regions (Depicker et al., *Mol. and Appl. Genet.* 1:561-573 (1982)). See also, Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. EMBO J. 2:987-992(1983); methotrexate, Herrera Estrella et al. *Nature* 303:209-213(1983); Meijer et al. *Plant Mol. Biol.* 16:807-820 (1991); hygromycin, Waldron et al. *Plant Mol. Biol.* 5:103-108 (1985), Zhijian et al. *Plant Science* 108:219-227 (1995); streptomycin, Jones et al. *Mol. Gen. Genet.* 210:86-91(1987); spectinomycin, Bretagne-Sagnard et al. *Transgenic Res.* 5:131-137 (1996); bleomycin, Hille et al. *Plant Mol. Biol.* 7:171-176 (1990); sulfonamide, Guerineau et al. *Plant Mol. Biol.* 15:127-136(1990); bromoxynil, Stalker et al. *Science* 242:419-423 (1988); glyphosate, Shaw et al. *Science* 233:478-481(1986); and phosphinothricin, DeBlock et al. *EMBO J.* 6:2513-2518 (1987). The latter is the phosphinothricin acetyl transferase ("PAT") or maize optimized PAT or bar gene which confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal* vol. 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci USA* (1991) 88:4587-4591; Grotewold et al., *Cell* (1994) 76:543-553; Sidorenko et al., *Plant Mol. Biol.* (1999)39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed genes where plant cells transformed with the marker gene are red in color, and thus visually selectable (Dietrich et al. (2002) *Biotechniques* 2(2):286-293). Additional examples include a p-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129: 2703), which encodes an enzyme capable of oxidizing tyrosine to DOPA and dopaquinone, which in turn condenses to form the easily detectable compound melanin. Clearly, many such markers are available to one skilled in the art.

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci. USA* 86:6126-6130 (1989); potyvirus leaders, for example, TEV leader (Tobacco Etch Virus), Allison et al.; MDMV leader (Maize Dwarf Mosaic Virus), *Virology* 154:9-20 (1986); human immunoglobulin heavy-chain binding protein (BiP), Macejak et al. *Nature* 353:90-94 (1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) *Molecular Biology of RNA*, pages 237-256; and maize chlorotic mottle virus leader (MCMV) Lommel et al. *Virology* 81:382-385 (1991). See also Della-Cioppa et al. *Plant Physiology* 84:965-968 (1987).

The cassette can also contain sequences that enhance translation and/or mRNA stability such as introns. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, Zea mays Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3): 477-84; Sullivan et al., J. Biol. Chem. (1992) 267(26):18999-9004) and the like. One skilled in the art will readily appreciate the many options available in expressing a product to a particular organelle. For example, the barley alpha amylase sequence is often used to direct expression to the endoplasmic reticulum (Rogers, J. Biol. Chem. 260:3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing a stilbene. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the heterologous sequence. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, Bio/Technology 10:268 (1992); and Weising et al., Ann. Rev. Genet. 22: 421-477 (1988). For example, the DNA construct may be introduced into the genomic DNA of the plant cell using techniques such as microprojectile-mediated delivery, Klein et al., Nature 327: 70-73 (1987); electroporation, Fromm et al., Proc. Natl. Acad. Sci. 82: 5824 (1985); polyethylene glycol (PEG) precipitation, Paszkowski et al., EMBO J. 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, Mol. Gen. Genetics 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (Zea mays L.) mediated by Agrobacterium tumefaciens" Nature Biotechnology 14:745-750 (1996). The virulence functions of the *Agrobacterium tumefaciens* host will direct the insertion of the construct into the plant cell DNA when the cell is infected by the bacteria. See, for example Horsch et al., Science 233: 496-498 (1984), and Fraley et al., Proc. Natl. Acad. Sci. 80: 4803 (1983).

Standard methods for transformation of canola are described at Moloney et al. "High Efficiency Transformation of Brassica napus using Agrobacterium Vectors" Plant Cell Reports 8:238-242 (1989). Corn transformation is described by Fromm et al, Bio/Technology 8:833 (1990) and Gordon-Kamm et al, supra. Agrobacterium is primarily used in dicots, but monocots can be transformed by Agrobacterium. See supra and U.S. Pat. No. 5,550,318. Rice transformation is described by Hiei et al., "Efficient Transformation of Rice (Oryza sativs L.) Mediated by Agrobacterium and Sequence Analysis of the Boundaries of the T-DNA" The Plant Journal 6(2): 271-282 (1994, Christou et al, Trends in Biotechnology 10:239 (1992) and Lee et al, Proc. Nat'l Acad. Sci. USA 88:6389 (1991). Wheat can be transformed by techniques similar to those used for transforming corn or rice. Sorghum transformation is described at Casas et al, supra and sorghum by Wan et al, Plant Physicol. 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art. For a discussion of plant breeding techniques, see Poehlman (1995) *Breeding Field Crops*. AVI Publication Co., Westport Conn., 4th Edit. Backcrossing methods may be used to introduce a gene into the plants. This technique has been used for decades to introduce traits into a plant. An example of a description of this and other plant breeding methodologies that are well known can be found in references such as Poelman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Scale up of the production of stilbenoids from hairy root cultures may be achieved by any of the known systems for plant propagation, and the invention is not limited by the means of increasing production of resveratrol and other stilbenes. For example, an airlift mesh-draught is one example (Caspeta et al. 2005); another uses a mesh support system (Ramakrishnan et al., 2004). A bioreactor system is further described below. One skilled in the art appreciates that there are many variations on the components and processes with which the nucleotide sequence of the invention may be used. The following is intended to be illustrative without limiting the scope of the invention.

Example 1

Producing Resveratrol and Resveratrol Derivatives from Peanuts

Materials and Methods

Establishment of hairy root cultures. Seeds of peanuts (*Arachis hypogaea*) cvs. Andru II and Hull (kindly provided by Dr. Daniel Gorbet, University of Florida) were surface sterilized as follows. Seeds were presoaked for 2 minutes in sterile water containing 0.003% Ivory™ detergent; immersed for 15 minutes in sterilization solution (50% Clorox™, 0.003% Ivory™ detergent) and rinsed in sterile water. To minimize Clorox™ damage to the embryo, the test was aseptically removed and seeds were further rinsed in two changes of sterile water over a 15 minute period. Disinfected seeds were placed individually on plates containing B5 medium to allow emergence of the radicle and to screen for viable healthy seedlings. Germinated seedlings were transferred to Magenta™ boxes containing B5 medium and allowed to grow in continuous light at 28° C. for 15 to 21 days. Explants used for hairy root production were harvested following expansion of two true leaves.

Cotyledon, hypocotyl, leaf blade, stem and petiole explants were evaluated. Whole, intact plantlets were also tested. Cotyledonary-node explants were later substituted for excised cotyledons. Intact seedlings and isolated explants were then evaluated for response to *Agrobacterium* infection. Three strains of *Agrobacterium* were tested: *A. rhizogenes* ATCC 15834, *A. rhizogenes* R1000 and *A. tumefaciens* EHA105 containing pRYG (containing rolA, rolB and rolC genes, Komarnytsky et al., 2004) plasmid. The latter plasmid was kindly provided by Dr. Ilya Raskin (Rutgers University, New Jersey) and mobilized into *A. tumefaciens* by freeze-thaw method (Holsters et al., 1978). Intact seedlings were inoculated with agrobacteria at the stem, petiole, or cotyledonary node. All other isolated explants were inoculated via epidermal incisions as described before (Medina-Bolivar et al., 2003; Medina-Bolivar and Cramer, 2004). Inoculated intact seedlings and explants were maintained in B5 medium plates under constant light at 28° C. Hairy roots developed at the inoculation site were harvested and transferred to B5 medium plates containing 600 mg/l cefotaxime, and maintained at 28° C. under continuous darkness. Roots were subcultured twice in this medium prior to transfer to antibiotic-free medium. Liquid hairy root cultures were established by inoculating ten 1-cm root tips into 250 ml flasks containing 50 ml of B5 medium. Roots were subcultured every 2 weeks and maintained on an orbital shaker at 90 rpm, 28° C. and continuous darkness.

Elicitation of hairy root cultures. Twelve-day peanut hairy root cultures were incubated for 24 hours in fresh B5 medium containing one of the following elicitors: 1 mg/ml laminarin, 1 or 10 µg/ml cellulase, 10 mg/L chitosan, 600 µM copper sulfate or 2.3 mg/ml (10.2 mM) sodium acetate. All elicitors were dissolved in water and filter sterilized, except for chitosan which was dissolved in 1 M acetic acid. Following elicitation, all media was collected and frozen at −20° C. All root tissue was collected, fresh weight recorded and roots then rapidly frozen in liquid nitrogen prior to storage at −80° C. Controls included hairy root cultures incubated 24 hours with equivalent volumes of water or acetic acid as well as non-elicited media samples collected from the 12-day hairy root cultures prior to initiating the elicitation procedure. To address expression kinetics of resveratrol in the hairy root system, 15-day hairy root cultures were elicited with 2.3 mg/ml (10.2 mM) sodium acetate for 0, 24, 48 or 72 hours. Media and root tissue were collected, processed and stored as outlined above.

PCR analysis The *A. rhizogenes* transferred genes rolC and aux1 were used as targets for PCR analyses in peanut hairy roots, whereas virD2 gene was used to detect for the presence of contaminating agrobacteria in the tissue. Genomic DNA from four hairy roots lines (2, 3, 5 and J-pRYG) of cv. Andru II were obtained using the DNeasy® Plant Mini kit (Qiagen, USA). A primer pair of 5'-TGTGACAAGCAGCGAT-GAGC-3' (SEQ ID NO: 1) and 5'-GATTGCAAACTTG-CACTCGC-3' (Bonhomme et al., 2000) (SEQ ID NO: 2) was used to amplify a 487-bp fragment of the rolC gene (Slightom et al., 1986) and a second pair of primers, 5'-CCAAGCTTGT-CAGAAAACTTCAGGG-3' (SEQ ID NO: 3) and 5'-CCG-GATCCAATACCCAGCGCTTT-3' (SEQ ID NO: 4) was designed to amplify a 815-bp fragment of the aux1 gene (GenBank accession No. DQ782955). In addition, primers (5'-ATGCCCGATCGAGCTCAAGT-3' (SEQ ID NO: 5) and 5'-CCTGACCCAAACATCTCGGCT-3' (SEQ ID NO: 6)), amplifying a fragment of 338 bp (Haas et al., 1995) were used for detecting the virD2 gene. The reactions were performed with puReTaq Ready-To-Go PCR beads (Amersham Biosciences, USA) containing 180 ng plant genomic DNA (or 10 ng Ri plasmid DNA) and 0.3 µM of each primer. Conditions for rolC amplification were as follows: initial denaturation at 95° C. for 3 minutes, 30 cycles of amplification (95° C. 30 s, 49° C. 30 s and 72° C. 1 min) and 10 minutes extension at 72° C.; for aux1, initial denaturation at 95° C. for 3 minutes, 30 cycles of amplification (95° C. 30 s, 58° C. 30 s and 72° C. 1 min) and 72° C. for 10 minutes; for virD2, initial denaturation at 95° C. for 3 minutes, followed by 30 cycles of amplification (95° C. 30 s, 56° C. 30 s and 72° C. 45 s) and 10 minutes at 72° C. PCR amplicons were visualized after electrophoresis in 0.7% agarose gels.

Extraction of resveratrol from culture medium. Media samples were thawed (50 ml) and partitioned with 30 ml ethyl acetate in a separatory funnel. The organic phase was recovered and dried to completeness under nitrogen stream using a RapidVap $N_2$ evaporation system (Labconco) at 40° C. and 40% rotor speed. These dried samples were resuspended in 50 µl of ethyl acetate for further analysis.

Qualitative TLC analysis. Aliquots of the extracts and pure, authentic standards of trans-resveratrol (Sigma Co, St. Louis, Mo.), polydatin—same chemical as piceid—(ChromaDex, Santa Ana, Calif.), pterostilbene (Sigma) and piceatannol (Sigma) were spotted on a 20×20 cm silica gel 60 $CF_{254}$ TLC plates (Merck) or a 10×10 silica gel 60 $CF_{254}$ HPTLC plates (Merck). Linear ascending development of the samples was carried out using a mobile phase of ethyl acetate:acetic acid:water (17:1:2) as described by Nepote et al., 2004. Plates were air dried and visualized under UV light (254 and 365 nm) using a Chromato-Vue® C-75 dark cabinet operated by CameraWindows-Canon PowerShot G6 software version 5.0.0.15.

Quantitative HPLC analysis. High performance liquid chromatography was carried out using an Agilent Series 1200 HPLC system equipped with quaternary pump, solvent degasser, autosampler with temperature controlled tray, column oven and diode array detector. The solvent system used was slightly modified from that reported by Jeandet et al. (2002) by extending the final analysis time at maximum % B solvent (see below). A Phenomenex Luna C-18 column (25 cm×0.49 cm i.d., 5 µm particle size equipped with a guard column) was run at a flow rate of 1.2 ml/min. Detection wavelength was at 280 nm with the spectrum from 190-800 nm collected.

The solvent gradient consisted of A; water:acetonitrile:o-phosphoric acid (95.45:4.5:0.05::v:v:v) and B: water:acetonitrile:o-phosphoric acid (49.95:50:0.05::v:v:v). The gradient used was as follows (all at 1.2 ml/min):

| Time | % A |
|---|---|
| 0 | 100 |
| 2 | 100 |
| 4 | 96 |
| 24 | 80 |
| 48 | 60 |
| 57 | 0 |
| 67 | 0 |
| 70 | 100 |
| 80 | 100 |

Freeze dried samples were reconstituted with 500 µl methanol, with vortex and ultrasonic treatments to ensure solubilization. Fifty µl injections were preformed in duplicate. All samples and standards were held at 5° C. during analysis in amber vials flushed with nitrogen gas before sealing.

Cis-resveratrol standard was prepared by exposing a methanolic solution of trans-resveratrol to outdoor noon sunlight for three hours in glass tube, flushed with nitrogen gas.

Quantitative analysis of resveratrol and pterostilbene by GC-MS. Dried medium or root tissue extracts (0.1 mg) were derivatized with 500 µL of a mixture of bis (trimethylsilyl) trifluoroacetamide:dimethyl formamide (1:1), heated at 70° C. for 40 min. After cooling to room temperature, samples were analyzed by gas chromatography/mass spectrometry (GC-MS) on a JEOL GCMate II system (JEOL USA, Inc., USA). The GC temperature program was as follows: initial temperature 190° C., then increased to 239° C. at a rate of 20° C./min and held at this temp for 3 minutes, then increased to 242° C. at a rate of 0.2° C./min and held at this temp for 4 minutes, then finally increased to 300° C. at a rate of 40° C./min and held at this temperature for 0.4 minutes (total run time 26 minutes). The GC capillary column used was DB-5 (0.25 mm i.d., 0.25 mm film thickness, 30 m length; Agilent Technologies, USA). The carrier gas was ultra high purity helium (nexAir, USA), 1 mL/min flow rate. The inlet (splitless), GC interface, and ion chamber temperatures were 250° C., 250° C., and 230° C., respectively. The injection volume was 2 µL.

Results and Discussion

Figure 3:
FIG. 3 shows hairy roots of peanut cv. Andru II initiated from stem explants.

Establishment of peanut hairy root lines for resveratrol production. Included among a divergent group of plants reported to have endogenously high levels of resveratrol are peanut roots (Chen et al., 2002), therefore this study targeted two independent cultivars of peanuts from which hairy root cultures were established. Explants harvested from 15- and 21-day old seedlings of peanut cvs. Andru II and Hull were used in establishing hairy root lines. While both Andru II and Hull yielded successful cultures, cv. Hull, while producing hairy roots, proved more problematic with only one explant resulting in the hairy root phenotype. A minimum of one explant for each type (stem, leaf, petiole, hypocotyls, cotyledon) in cv. Andru II successfully responded with a hairy root phenotype. Generally, the peanut hairy roots derived from both varieties initiated as early as 14 days after inoculation (FIG. 3), gave an average root thickness of 1 mm, were highly branched with no apparent root hairs and showed plagiotropic growth. Interestingly, the absence of root hairs have been observed in other *A. rhizogenes*-derived roots from legumes such as alfalfa, as well as species from other families such as *Trichosanthes kirilowii* (Savary and Flores, 1994). Whole intact seedlings inoculated on tissues held above the media surface were less successful, and were slower to respond. In addition, harvested explants of small size or slender mass (petioles and young expanding leaf blades) yielded fewer roots and grew more slowly.

Due to the fact that various plants can exhibit differential susceptibility to the *Agrobacterium rhizogenes* strain, a number of different strains for generating peanut hairy root lines were tested. Of the two *A. rhizogenes* strains tested (R1000 and ATCC 15834) ATCC 15834 was successful in providing the most consistent hairy root responses. *A. tumefaciones* EHA105 containing the pRYG was successful in the initiation of hairy roots, however these roots did not provide optimum proliferation in liquid cultures and proliferation in subcultures was not maintained. Strain ATCC 15834 was used in the successive experiment. When the experiment was repeated using younger explants (15-day old seedlings) the results for both cultivars, Andru II and Hull, improved (Table 1).

TABLE 1

Response of different explants of peanut cvs. Andru II and Hull to inoculation with *Agrobacterium rhizogenes* 15834. Explants were taken from 15-day old seedlings.

| | petiole | stem | cot-node | hypocotyl |
|---|---|---|---|---|
| ANDRU-II | | | | |
| | C | C | HR | NR |
| | C | C | HR | NR |
| | HR | C | HR | HR |
| | HR | C | HR | C |
| | C | HR | HR | NR |
| | HR | HR | HR | C |
| | C | NR | HR | C |
| | HR | C + RI | HR | HR |
| | HR | C | HR | C |
| | HR | C + HR | HR | HR |
| Explants with HR response | 60% | 30% | 100% | 30% |
| Hull | | | | |
| | C | C | HR | HR |
| | C | HR | HR | NR |
| | C | NR | HR | HR |
| | C | NR | HR | NR |
| | C | NR | HR | HR |
| | C | C | HR | HR |
| | C | HR | HR | NR |
| | C | HR | HR | NR |
| | HR | HR | HR | C |
| Explants with HR response | 10% | 50% | 100% | 40% |

C=callus response, HR=hairy root response, NR=no response, RI=root initial(s).

There was little difference in overall response between the two cultivars, but more explants of cv. Andru II were successful. It is of interest to note that for both peanut varieties, 100% of cotyledonary-nodes produced hairy roots. Isolated cotyledonary node tissue was more reliable than stem, petiole or hypocotyls section explants. These explants consistently responded with larger more prolific roots at the inoculation site. (Table 2)

TABLE 2

Response of peanut explants to inoculation with *Agrobacterium rhizogenes* 15834. Observations were made after 3 weeks. HR = Hairy root.

| Seedling number | Petiole | Stem | Cotyledonary node | Hypocotyl |
|---|---|---|---|---|
| 1 | HR | callus | HR prolific | no response |
| 2 | callus | callus | HR | no response |
| 3 | HR | callus | HR | HR |
| 4 | HR | callus | HR | callus |
| 5 | callus | HR | HR prolific | no response |
| 6 | HR | HR | HR | callus |
| 7 | callus | no response | HR prolific | callus |
| 8 | HR | HR + callus | HR prolific | HR |
| 9 | HR | callus | HR prolific | callus |
| 10 | HR prolific | HR + callus | HR | HR |

Cotyledonary node explants were an advantage for cv. Hull which responded with slightly lower frequency when stem, petiole and hypocotyl explants were used. After isolation on B5 medium, hairy root lines were tested for vigor, lines failing to sustain vigorous independent growth were discarded.

The advantage of hairy roots as a production source of resveratrol and other valued plant metabolites over in vitro cell culture systems (Bru et al., 2006) is that this tissue-based system captures the metabolic processes as they happen in nature. These roots reflect the metabolic phenotype of the host plant yet are unique in their genetic and biosynthetic stability and have the advantage of offering fast growth for generating the requisite biomass. Hairy roots take advantage of biotechnological techniques to provide an environmentally-friendly and resource-sparing production system for valued natural products that preserves biodiversity of native plant stocks which may be limited.

Figure 4:
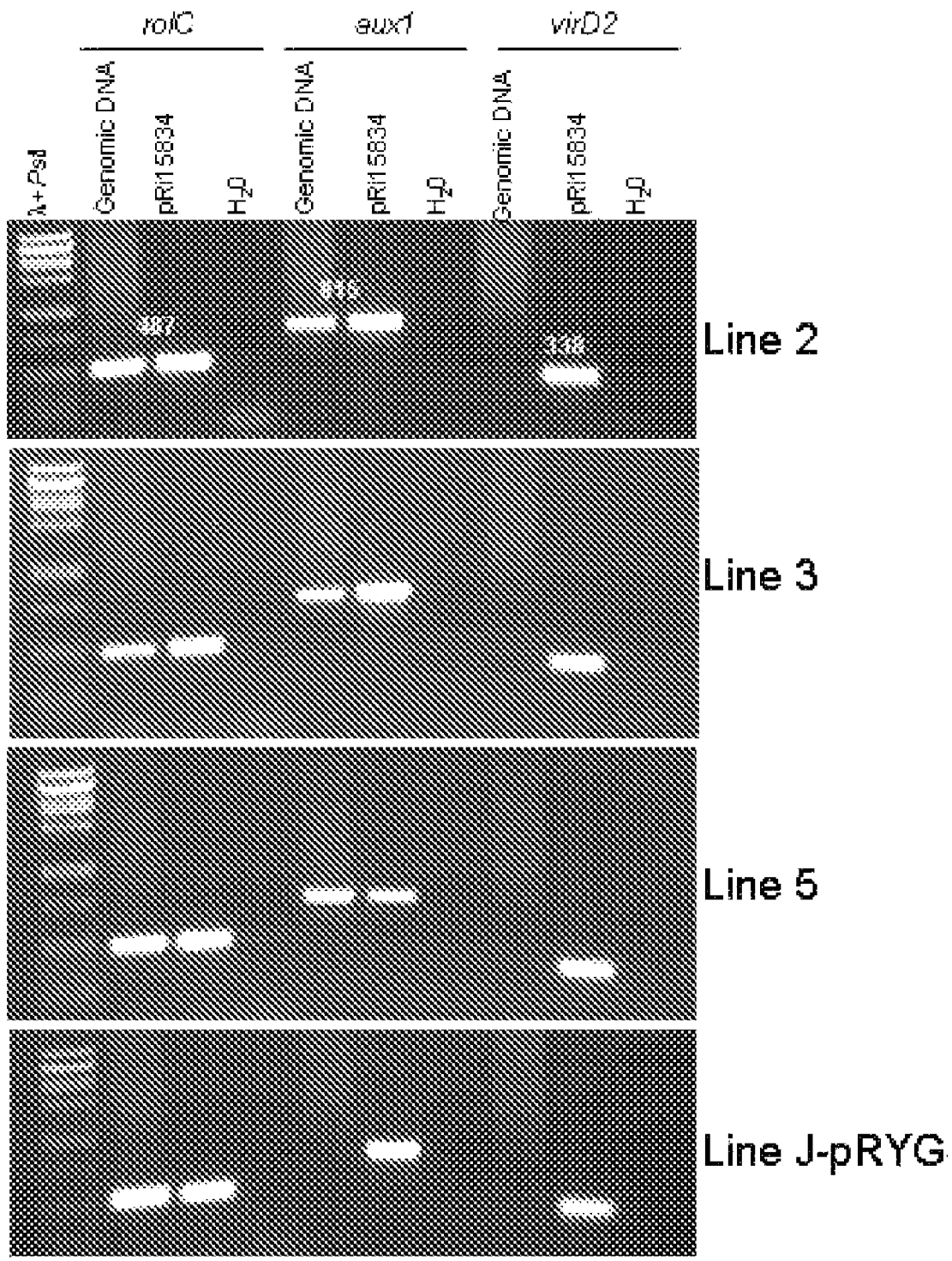
FIG. 4 shows analysis by PCR of hairy root lines.

PCR analysis of hairy roots In order to assess the genetic status of the hairy roots, a PCR-based analysis was used that targeted the *A. rhizogenes* rolC, aux1 and virD2 genes. The rolC and aux1 genes, located on independent T-DNAs (TL-DNA and TR-DNA, respectively) of the Ri plasmid of *A. rhizogenes* strain 15834, are diagnostic for T-DNA integration into the host genome. The virD2 gene, located outside the T-DNA, is diagnostic for the presence of any remaining agrobacteria in the root tissue. Three peanut hairy roots lines (2, 3, 5) showing the highest growth rates in liquid cultures as well as line J-pRYG exhibiting substandard growth were analyzed. Analyses were performed with primers targeting rolC, aux1 and virD2 genes. Plasmid pRi15834 DNA was used as a positive control. While both rolC and aux1 genes were detected in hairy root lines 2, 3 and 5, only the rolC gene was identified in line J-pRYG (FIG. 4). The coexistence of the rolC and aux1 genes indicated that hairy root lines 2, 3 and 5 successfully integrated both the TL-DNA (Slightom et al., 1986; Schmülling et al., 1988) and the TR-DNA (Camilleri and Jouanin, 1991) of the pRi15834 plasmid. While initiation of hairy roots in peanut explants was also achieved in the absence of aux genes (i.e. line J-pRYG), these roots did not sustain growth in successive subculturing. Similar responses were observed with other lines peanut developed with the pRYG vector, suggesting gene products of both the TL-DNA and TR-DNA are needed to establish high biomass yielding peanut hairy roots. This observation is consistent with the studies of Komamytsky et al. (2004), where it was reported that indole-3-acetic acid supplementation was needed to support the growth of tobacco hairy roots established with the pRYG vector that only contains rol genes. More studies with different hairy root lines from different plants species will be needed to confirm the contribution of aux genes in promoting hairy root growth. No peanut hairy roots lines analyzed carried the virD2 gene (FIG. 4) indicating the absence of *A. rhizogenes* ATCC 15834 contamination in these cultures. High biomass accumulation, sustainable growth following several subculture events and T-DNA integration were used as the selection criteria in assigning peanut hairy roots lines 2, 3, and 5 of cv. Andru II as the lead production lines for further analysis.

Figure 5:
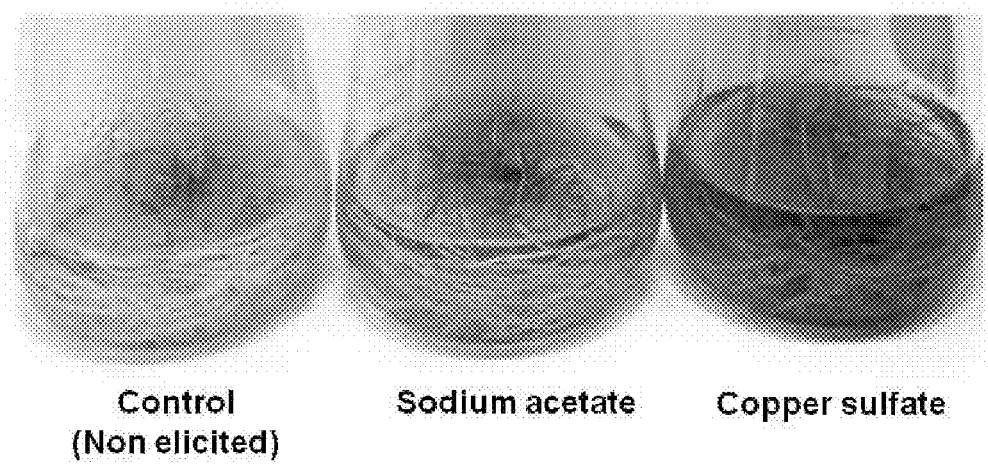
FIG. 5 shows results of elicitation of hairy root cultures of peanut cv. Andru II. Twelve-day cultures were elicited for 24 hours with 2.3 mg/l (10.2 mM) sodium acetate or 600 µM copper sulfate.

Elicitation of peanut hairy roots. Initially, five elicitors were tested at different concentrations for induction of resveratrol. These included: cellulase, laminarin, chitosan, sodium acetate, and copper sulfate. Four hairy roots lines (2, 3, 5 and 6) of cv. Andru II showing the highest root growth were studied. The elicitors were applied to the root cultures for 24 hours. Some elicitors provoked a strong reaction in the hairy root cultures, resulting in color change of the root tissue and medium (FIG. 5). Notably, copper sulfate induced the browning on the tissue and of the medium suggesting the production and secretion of phenolics. Sodium acetate elicitation did not affect the color of the roots, however a slight yellowish color of the medium was observed. The other tested elicitors did not seem to affect the color of the tissue or medium.

Figure 6:
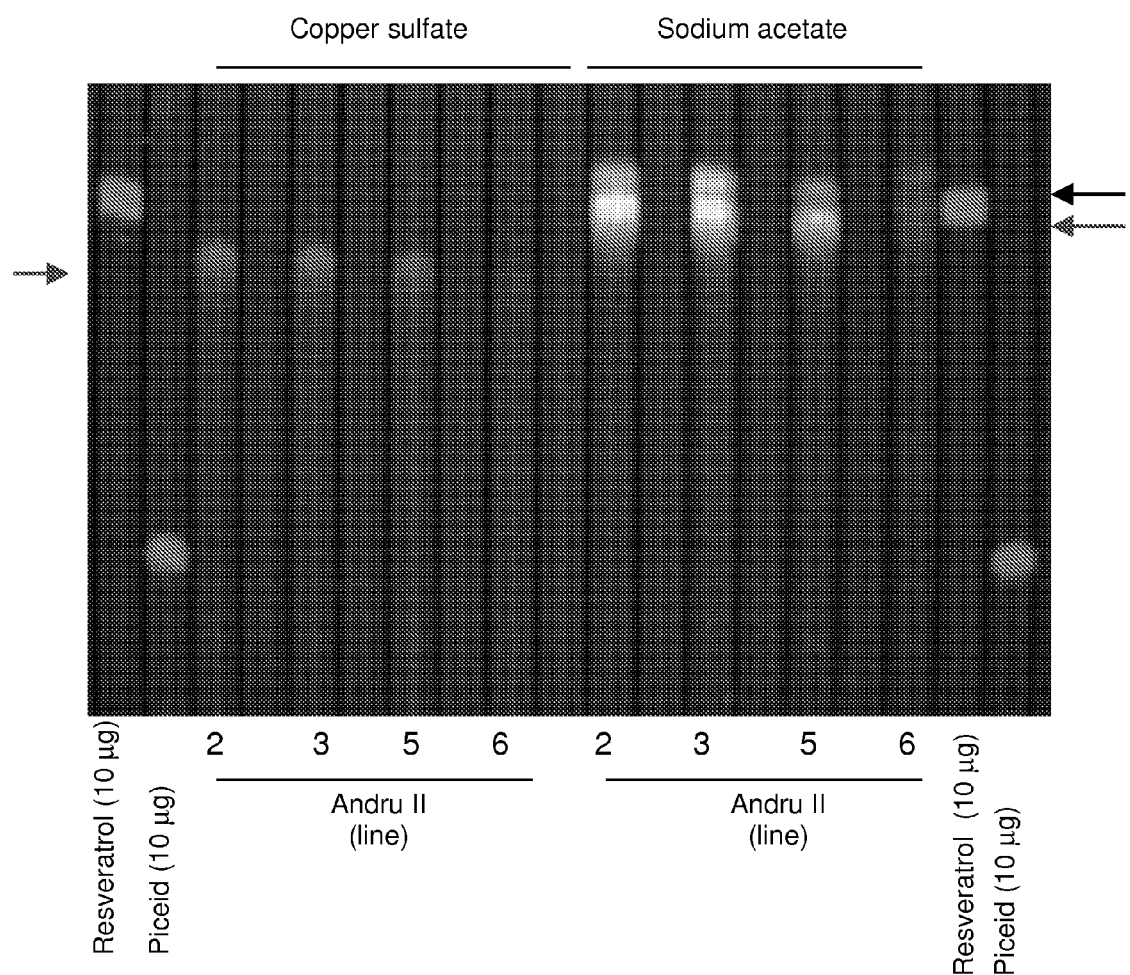
FIG. 6 shows thin layer chromatography of ethyl acetate extracts from peanut hairy root culture medium. Twelve-day cultures were elicited for 24 hours with either 600 µM copper sulfate or 2.3 mg/l (10.2 mM) sodium acetate. Reference standards: trans-Resveratrol (10 µg) and piceid (10 µg).

Qualitative analyses of elicited peanut hairy root cultures. In an effort to rapidly assess the various hairy root lines for resveratrol production and secretion into the culture medium, we adapted a thin layer chromatographic method (TLC) that leverages the fluorescent nature of resveratrol at defined excitation wavelengths (Nepote et al., 2004). In a preliminary experiment, the culture medium was lyophilized to completeness and the dried medium was resuspended in methanol. This extract produced a very viscous solution which was difficult to resolve by TLC. In addition, the high content of carbohydrates in this sample appeared to bind the phenolic compounds (i.e. resveratrol). In an effort to overcome these issues, we optimized the purification of resveratrol in the culture medium by determining the solubility of resveratrol in various organic solvents. Ethyl acetate showed good solubility of resveratrol and was not miscible with the culture medium phase thus facilitating efficient resveratrol recovery. Initial analyses of the ethyl acetate extracts of hairy root media were compared by TLC to pure authentic references standards of trans-resveratrol and piceid. As shown in FIG. 6, copper sulfate and sodium acetate elicitation induced production of blue fluorescent compounds under excitation with UV light (365 nm) in all the peanut cv. Andru II hairy root lines tested. The strongest fluorescent chemical was detected in the medium of sodium acetate-elicited hairy roots and generated an Rf of 0.83 corresponding to that of authentic trans-resveratrol. Elicitation of hairy root lines with copper sulfate induced production of a fluorescent compound at Rf 0.73 thus being a product of different polarity than trans-resveratrol. Observation under UV light (254 nm) showed the characteristic dark spots (with a green fluorescent background) for the standards and products produced in the hairy root cultures. From this initial assessment, we successfully established a number of peanut hairy root lines that effectively secreted measurable levels of trans-resveratrol.

Figure 7:
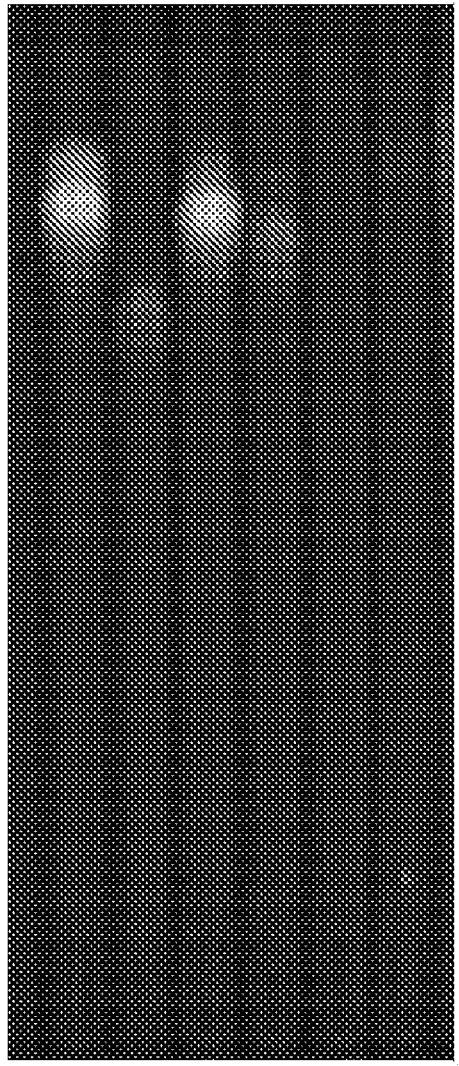
FIG. 7 shows thin layer chromatography of ethyl acetate extracts from peanut cv. Andru II culture medium of line 2. Twelve-day cultures of were elicited for 24 hours with 10 µg/ml cellulase, 1 mg/ml laminarin, 10 mg/l chitosan, 600 µM copper sulfate, 1 mg/ml laminarin or 2.3 mg/ml sodium acetate. Control; non elicitation. Standards: trans-resveratrol (2 µg), pterostilbene (10 µg), piceid (10 µg) and piceatannol (2 µg).
Figure 7:
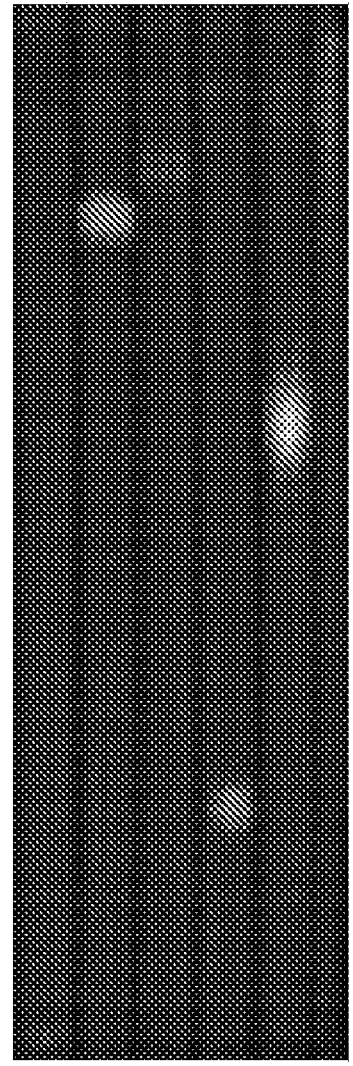

In an effort to identify the most effective elicitor in secreting resveratrol from hairy root cultures, we tested five elicitors independently on a sodium acetate responsive 12-day hairy root line (line 2). Four reference standards (trans-resveratrol, piceid, piceatannol and pterostilbene) were run on TLC plates along with elicited hairy root media samples. Four of the five elicitors tested generated fluorescent detectable products as shown in FIG. 7. Sodium acetate (2.3 mg/L; 10.2 mM) induced two products, one with a strong fluorescent signal corresponding to the Rf of the trans-resveratrol standard (0.86) and a second product with Rf 0.91 corresponding to pterostilbene. Chitosan (10 mg/L) induced the two products as observed for sodium acetate elicitation, however the pterostilbene corresponding product was of lower fluorescence intensity. Copper sulfate induced a fluorescent chemical of Rf 0.73 while laminarin induced production of a blue fluorescent chemical with an Rf 0.78 neither of which corresponded to any of the standards included in this analysis. It is worth noting that the Rfs of the piceid and piceatannol references were 0.26 and 0.69, respectively, which were not secreted by this peanut hairy root line. In light of the fact that trans-resveratrol is the desired product and piceid is recognized as a less bioactive form of resveratrol, peanut hairy roots provide a novel trans-resveratrol-enriched production system. Finally, no fluorescent chemicals were detected in the ethyl acetate extracts of non-elicited samples nor cellulase-elicited media samples (at either 1 or 10 μg/ml) (FIG. 7) again supporting elicitor-selective production of resveratrol in these hairy root lines. Determinations were recorded every three days.

HPLC analyses of induced hairy root culture medium. To quantitate and confirm the presence of resveratrol, we analyzed trans-resveratrol-producing hairy root media samples using high performance liquid chromatography (HPLC) based on UV absorption. Trans-resveratrol alone or mixed with other phenolic standards were analyzed to establish a reference standard chromatographic profile.

Figure 8:
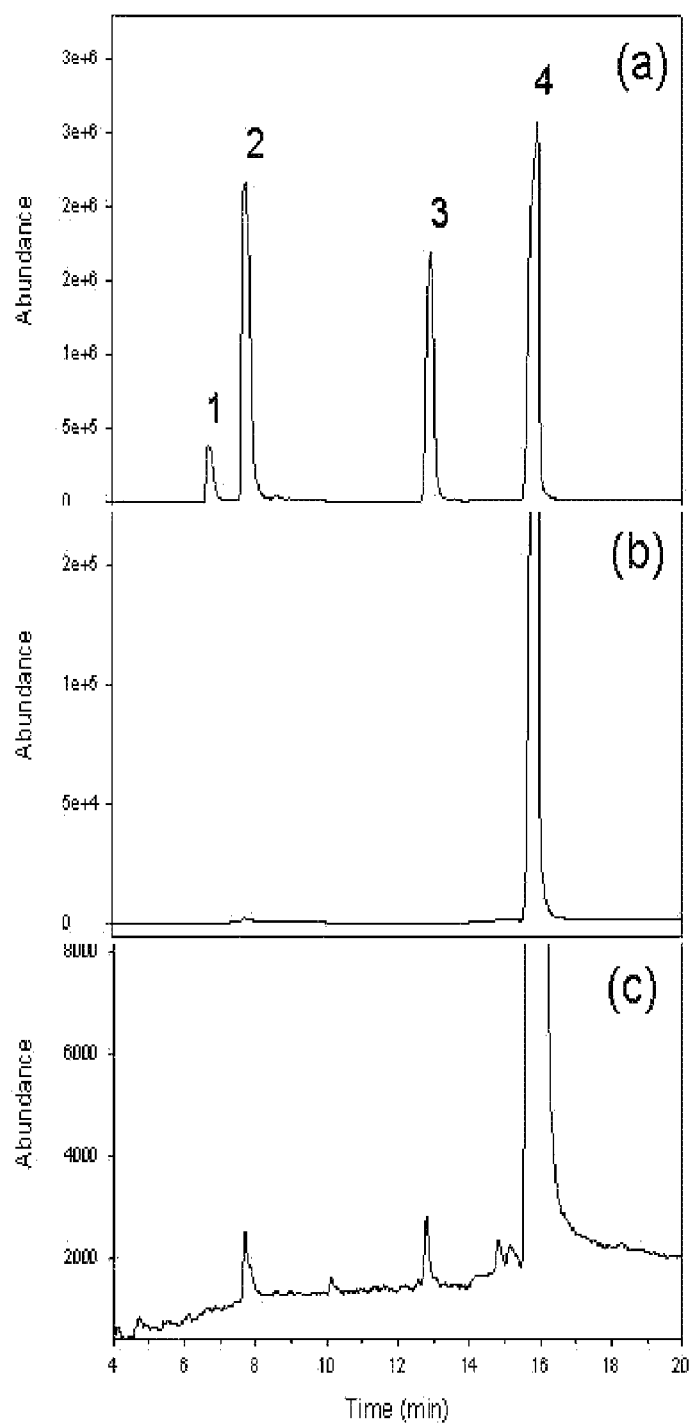
FIG. 8 shows (a) GC-MS trace of mixture of cis-pterostilbene (peak 1, 6.6 mill; $[M]^+$-TMS m/z 328), cis-resveratrol (peak 2, 7.7 mill; $[M]^+$-TMS m/z 444), trans-pterostilbene (peak 3, 13.0 mill; $[M]^+$-TMS m/z 328) and trans-resveratrol (peak 4, 16.0 mill; $[M]^+$-TMS m/z 444); (b) GC-MS trace of ethyl acetate extract from the medium of sodium acetate-elicited culture showing peak of trans-resveratrol; (c) reconstructed ion chromatogram from the GC-MS analysis of the medium of sodium acetate-elicited culture showing the peaks of cis- and trans-resveratrol, and of trans-pterostilbene (cis-pterostilbene was lot found).

Quantitative analysis of resveratrol and pterostilbene by GC-MS. Analysis of cis- and trans-resveratrol and cis- and trans-pterostilbene was carried out in a selected ion monitoring mode (retention times 7.7, 15.7, 6.6. and 12.8 mm, respectively; FIG. 8). Cis- and trans-resveratrol were monitored for m/z 444 (and 429, 207, 147 as qualifier ions). Cis- and trans-pterostilbene were monitored for m/z 328 (and 313, 296, 156 as qualifier ions). Quantitation was performed using external standards of a commercial sample of trans-resveratrol (Sigma) and a synthetic sample of trans-pterostilbene (synthesized from methylation of resveratrol). The cis isomers were obtained by UV-irradiation (λ 306 nm) of an ethanolic solution the trans isomers (1 mg/mL) for 24 hours.

Figure 9:
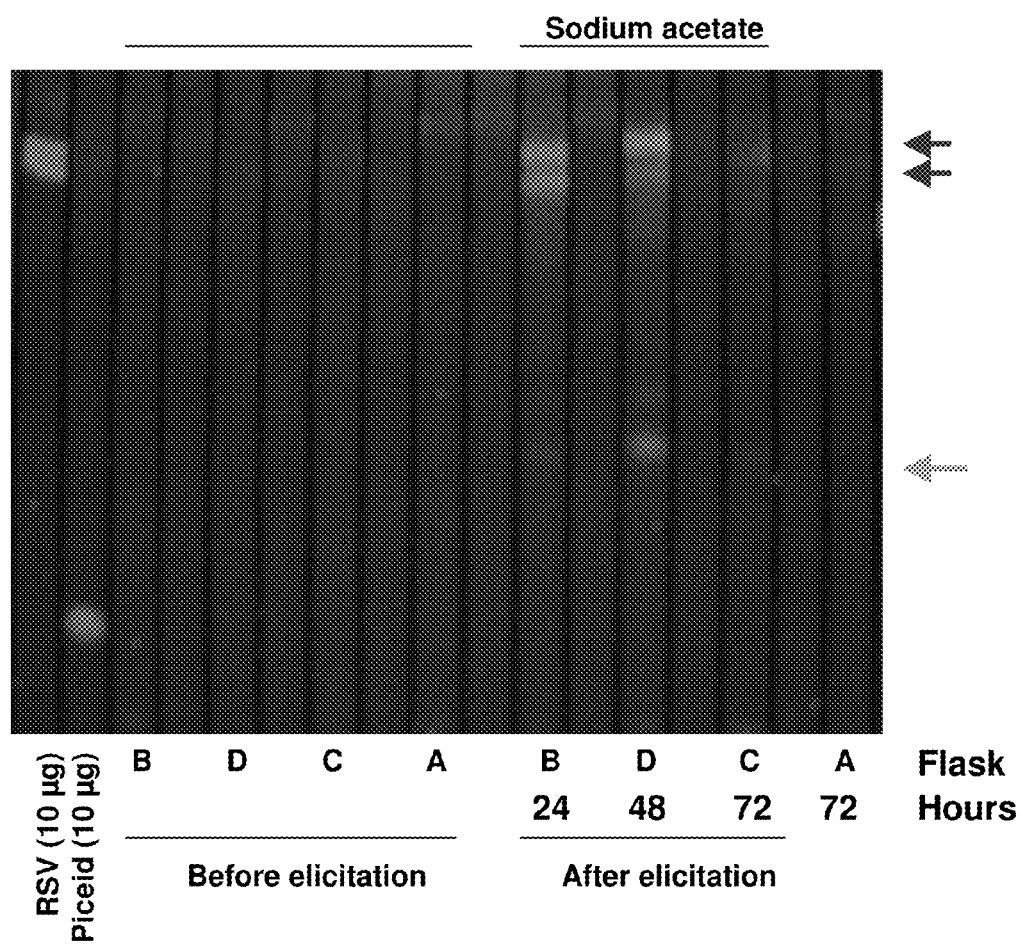
FIG. 9 shows time course of resveratrol accumulation in hairy root culture medium. Ethyl acetate extracts from 15-day hairy root culture medium of peanut cv. Andru H (line 2) were prepared after 24, 48 and 72 hours of elicitation with sodium acetate and analyzed by thin layer chromatography. Reference standards: trans-resveratrol (10 µg) and piceid (10 µg).

Time course of accumulation of trans-resveratrol in culture medium. To determine the kinetics of resveratrol accumulation into the culture medium in an effort to better define optimal culturing conditions, peanut hairy root culture line 2 was elicited with sodium acetate and media was collect at 24, 48 or 72 hours after elicitation. We evaluated 15-day cultures instead of 12-day to determine the impact of the culture age on elicitation response time. As observed in FIG. 9, the two major fluorescent products observed corresponding to trans-resveratrol and putative pterostilbene for the elicited 12-day cultures were detected in 15-day culture media following 24 hour elicitation. At 48 hours, the presence of resveratrol was decreased while pterostilbene levels increased. This is consistent with pterostilbene being a downstream product of this biosynthetic pathway. Interestingly a product of green fluorescent with a lower Rf than resveratrol began to accumulate at 48 hours as well. Both trans-resveratrol and pterostilbene levels decreased at 72 hours post elicitation (FIG. 9).

Figure 10:
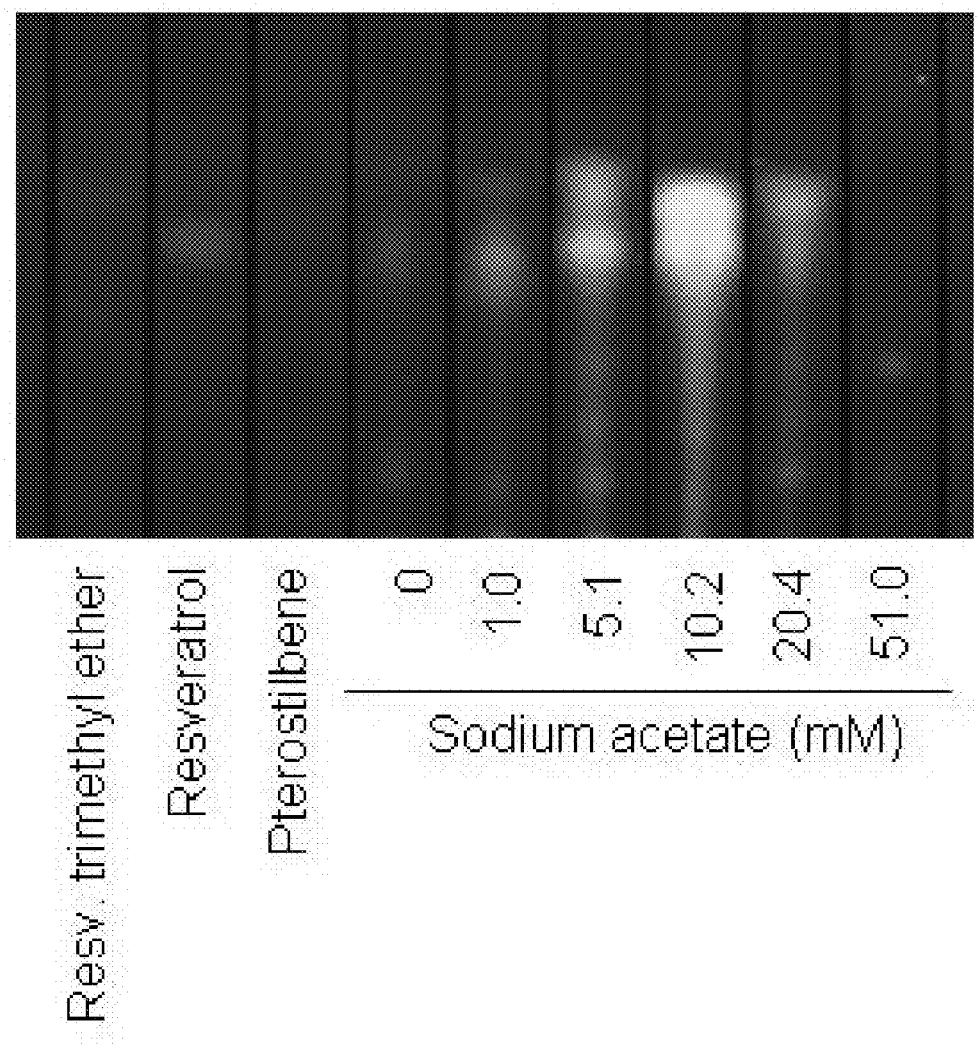
FIG. 10 shows HPTLC of ethyl acetate extracts from media of hairy root line 2 treated with varying amounts of sodium acetate.

Sodium acetate was chosen as the elicitor in all further studies. In addition to exhibiting marked induction of a product correlating with the Rf of trans-resveratrol, sodium acetate is cost-effective in consideration of the commercial scale-up of this system. Furthermore, we observed reproducible elicitation profiles in several, independently-generated hairy root lines. Line 2 which exhibited the highest response to sodium acetate elicitation, was selected for further investigation. A dose response indicated about 10 mM sodium acetate had the most effective response in producing compounds with Rf values in the range of resveratrol, pterostilbene and the more methylated resveratrol analog, resveratrol trimethyl ether. FIG. 10 shows effect of sodium acetate elicitation. HPTLC of ethyl acetate extracts from the media of hairy root line 2 treated for 24 hours with sodium acetate at 0 to 51 mM reflected that preferred amount of sodium acetate is about 5 to about 21 mM, with about 10 mM most preferred.

Figure 11:
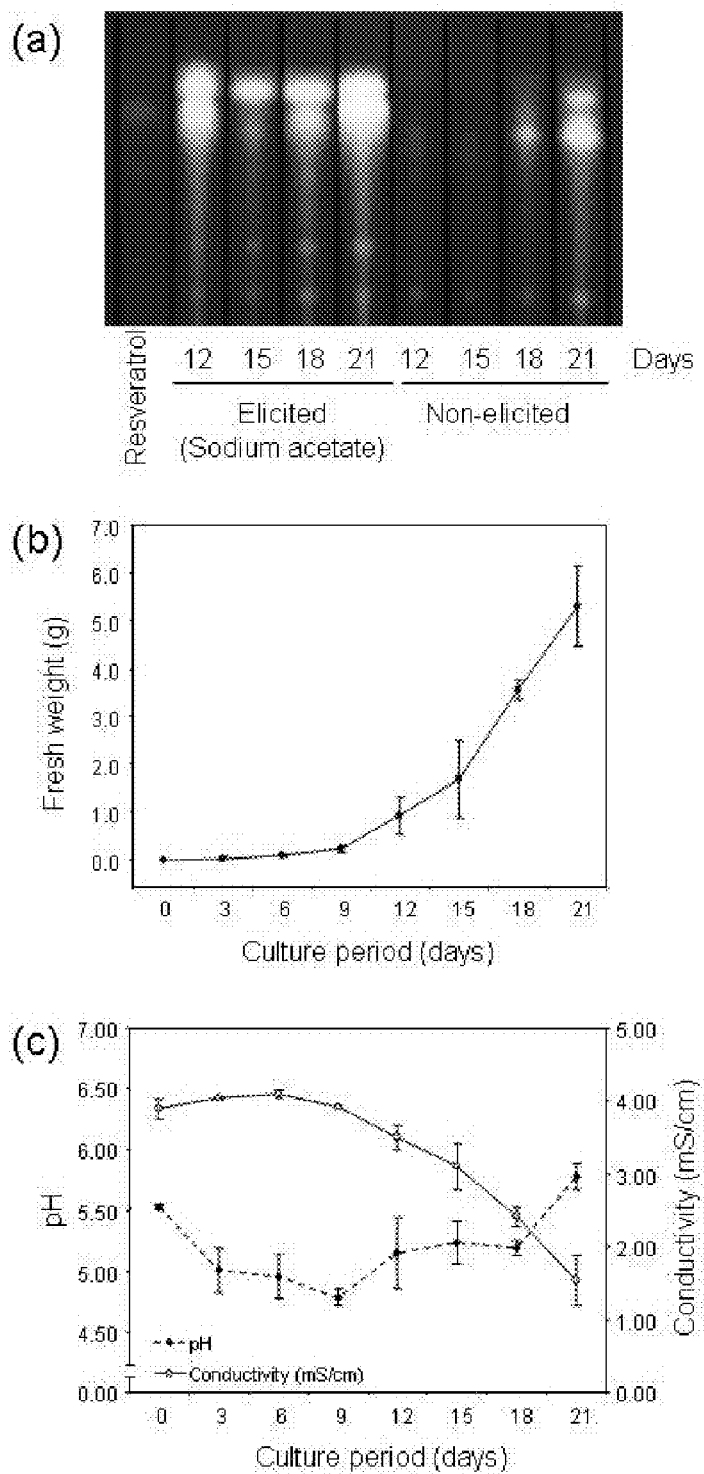
FIG. 11 shows (a) HPTLC of ethyl acetate extracts from the medium of hairy root line 2 treated with 10.2 sodium acetate at different stages of growth. Resveratrol (2 µg). Thirty five µg of extract were loaded per lane. (b) Growth curve of peanut hairy root line 2 in liquid B5 medium. (c) Measurements of medium conductivity and pH at different stages of growth.

A detailed growth curve and medium conductivity analysis of line 2 indicated that the culture was in an early exponential growth phase at the time of elicitation on day 12 (FIGS. 11A, 11B, and 11C). Because the effectiveness of an elicitor is likely impacted by the developmental stage of the culture (Pitta-Alvarez and Giulietti, 1999), we evaluated the sodium acetate response of the peanut hairy root culture at various time points across their growth cycle ranging from 12 through 21 days. Non-elicited root cultures of corresponding age served as controls. While no fluorescent compounds with the corresponding Rf of resveratrol were found by TLC in the medium of non-elicited 12- or 15-day cultures, products in this Rf range were detected in the medium from 18- and 21-day cultures suggesting that culture age impacts the production/secretion of these fluorescent compounds independent of elicitation. Moreover, the production and secretion of these compounds could be significantly induced throughout the exponential growth of the roots cultures. Elicitation profiles appeared to be biphasic with initial product induction observed early in exponential growth (12 days) and a second induction peak in late exponential growth (21 days). At 21 days, the amount of the observed secreted fluorescent compounds may represent a combination of both endogenously secreted and sodium acetate-elicited compounds.

Example 2

Figure 12:
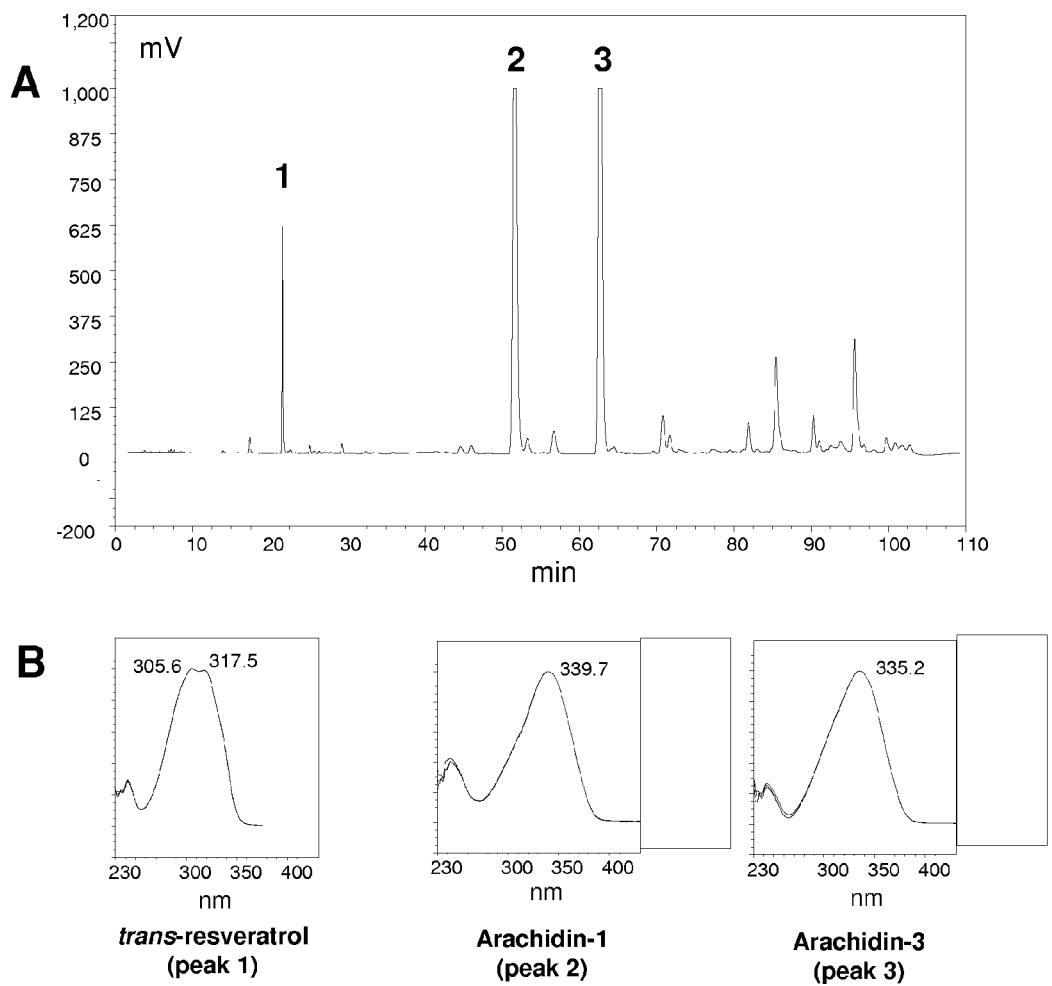
FIG. 12 are graphs showing HPLC analyses of the medium of elicited hairy root cultures of peanut cv. Andru II, line 2
Figure 13:
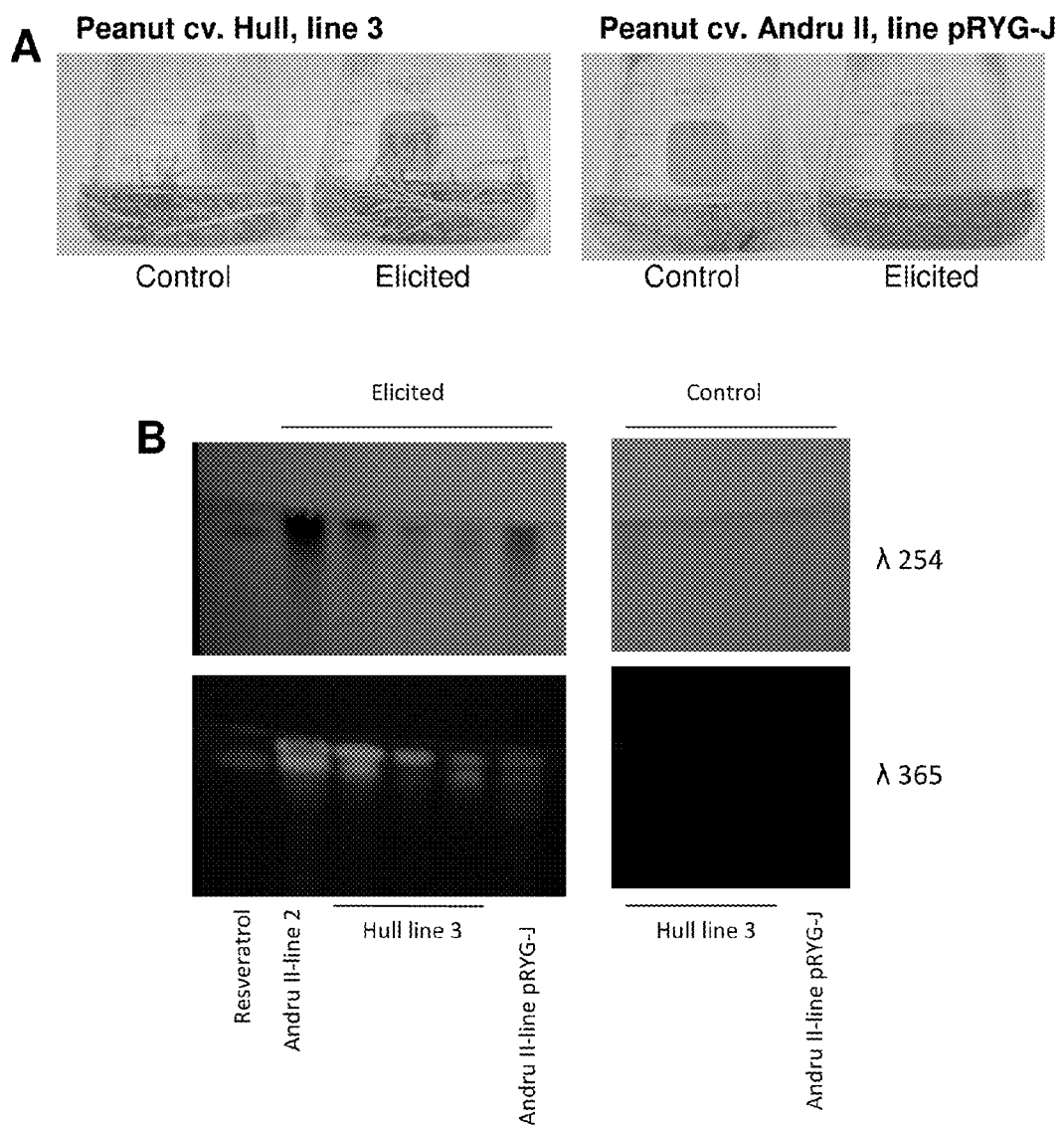
FIG. 13 shows elicitation of resveratrol and derivatives in hairy roots of peanut cv Andru II and Hull. A. Hairy root of peanut cv. Andru II (line pRYG-J) and cv. Hull (line 3). Hairy roots were cultured in B5 medium. B. HPTLC analysis of resveratrol and derivatives. Elicitation induced the production of resveratrol and derivatives. Analysis was done under UV light (254 and 365 nm).

Production of Resveratrol and Resveratrol Derivatives in the Peanut Cultivar, Hull Using the materials and methods outlined above, resveratrol and resveratrol derivatives were elicited in the peanut hairy roots derived from the Hull cultivar. Hairy root cultures were elicited for 24 hours with 10.2 mM sodium acetate and resveratrol and derivatives were extracted from the medium with ethyl acetate. Control roots were not elicited. See FIGS. 12 and 13. Elicited hairy root of peanut cv. Andru II (line pRYG-J) and cv. Hull (line 3) s were cultured in B5 medium. HPTLC analysis of resveratrol and derivatives is shown in the figure. Elicitation induced the production of resveratrol and derivatives. Analysis was done under UV light (254 and 365 nm).

Example 3

Production of Resveratrol and Resveratrol Derivatives in Grape

Figure 14:
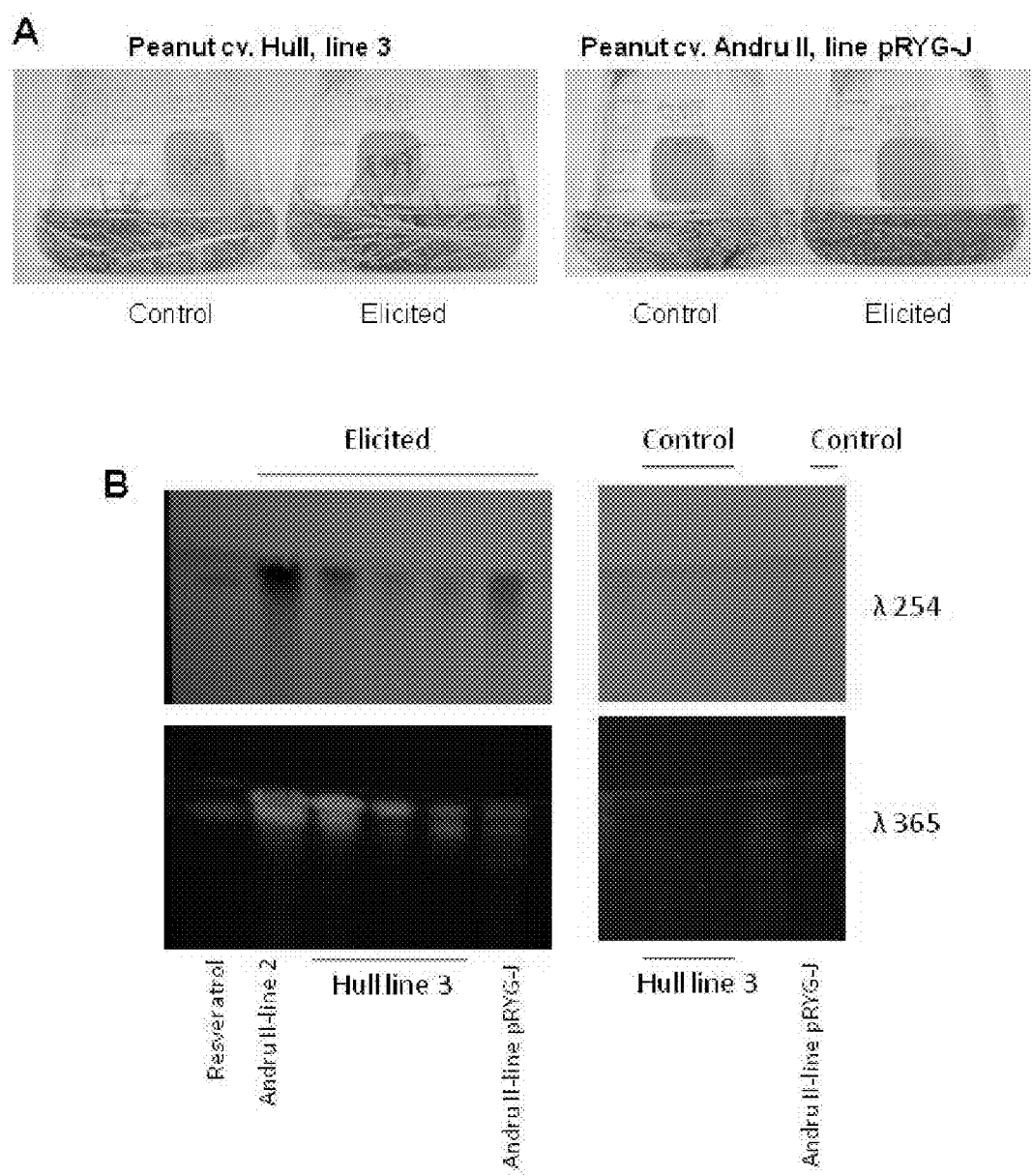
FIG. 14 shows elicitation of resveratrol and derivatives in hairy roots of muscadine grape. A. PCR analyses of hairy roots of muscadine grape (*Vitis rotundifolia*) cvs. Noble and Fry. Roots were analyses for the presence of rol C and aux 2 genes. B. Hairy of muscadine grape cv. Fry, line 3A. Hairy roots were cultured in B5 medium. C. HPTLC analysis of resveratrol and derivatives. Resveratrol was observed in low levels in control (non-elicited) cultures. Elicitation induced the production of resveratrol and derivatives. Analysis was done under UV light (365 nm).

Elicitation of resveratrol and derivatives in hairy roots of muscadine grape was achieved using the materials and methods outlined above. Cultures were elicited for 24 hours with 10.2 mM sodium acetate and resveratrol and derivatives were extracted from the medium with ethyl acetate. PCR analyses of hairy roots of muscadine grape (*Vitis rotundifolia*) cvs. Noble and Fry is shown in FIG. 14. Roots were analyzed for the presence of rol C and aux 2 genes. Hairy roots were cultured in B5 medium. HPTLC analysis of resveratrol and derivatives is shown in the figure indicating resveratrol and resveratrol glucosides. Resveratrol was observed in low levels in control non-elicited cultures. Analysis was done under UV light (365 nm).

Example 4

Infection of Plant Tissue with rol and aux Genes

Figure 15:
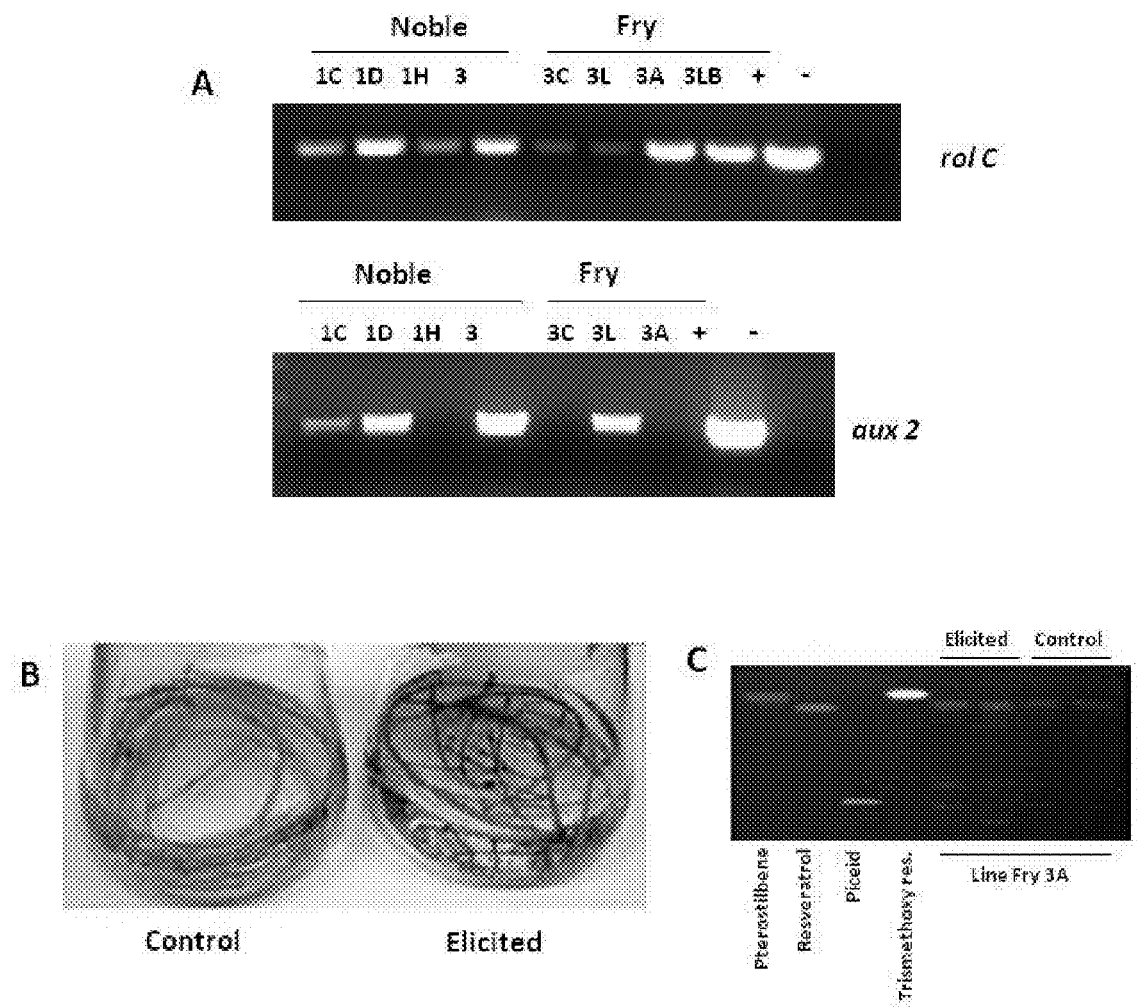
FIGS. 15 A-C shows the sequence of the cloned aux1 and aux2 genes (the aux1 and aux2 nucleotide sequence is SEQ ID NO: 7, the amino acid of aux2 is SEQ ID NO: 8, the amino acid of aux1 is SEQ TD NO: 9) and primer sequences used (SEQ ID NO: 10-17).

The above experiments are carried out using the single T-DNA containing the rol and aux genes in one vector and infected into plants via *Agrobacterium tumefaciens* as described supra. A vector containing the rolA, rolB and rolC from pRYG, described supra, is created, which also includes aux1, and aux2 genes, cloned by the inventors, and set forth in FIG. 15. (SEQ ID NO: 7, 8 and 9) along with the primers used (SEQ ID NO: 10-17.

The DNA sequence encoding for aux1 and aux2 genes were cloned by PCR from plasmid pRi 15834 (Ri plasmid of *A. rhizogenes* strain 15834). Primer sequences were designed from the non-translated region of homologous genes in plasmid pRi A4 (GeneBank accessions No. M61151, S62276, X15952). In addition, restriction sites KpnI were added at 5'-end in each primer. The PCR fragment obtained by Pfu polymerase using the primers mentioned above was ligated into KpnI site of pBC vector and sequenced to confirm for the aux1 and aux2 coding region. The cloned 4586 bp DNA sequence was deposited in the NCBI database, accession DQ782955 (Condori and Medina-Bolivar, 2006). To construct the binary vector with rol and aux genes, we used plasmid pRYG as recipient vector. This plasmid has the rolA, rolB and rolC genes as well as a multicloning site in the T-DNA. The KpnI site in pRYG's T-DNA region was used to ligate the cloned aux1 and aux2 DNA region. Ligation junctions were sequenced to confirm accuracy of ligation.

The engineered binary vector with the rol and aux genes contained in the same T-DNA was mobilized into *A. tumefaciens*. Because of the pRYG backbone in this vector, plasmid pSoup is required for amplification of the vector in *Agrobacterium*. Therefore plasmids pSoup and the engineered vector (with rol and aux genes) were co-introduced in *A. tumefaciens* strains LBA4404 and EHA105.

The transformed *A. tumefaciens* was then used to inoculate the midrib of tobacco leaf explants following an established transformation protocol (Medina-Bolivar and Cramer, 2004). Hairy roots developed at the inoculation site 2-3 weeks after inoculation.

In addition to the procedures described above, more than one line of hairy roots is screened to identify a line that is capable of sustaining growth in liquid following subculturing, in an auxin-free medium,

Example 5

Production of Stilbenes in *Nicotiana*

Establishment of Hairy Root of *Nicotiana benthamiana* and Elicitation of Pinosylvin and Derivatives Seeds of *Nicotiana benthamiana* were surface sterilized and germinated on MS semi-solid medium. Axillary nodes were harvested from the axenic seedlings and used to establish plantlets. The latter were then micropropagated in MS medium and leaves from these plantlets were used as explants for *Agrobacterium rhizogenes* inoculations. Leaves were harvested from 2-3 week old plantlets and placed on B5 medium. The leaves were inoculated in the midrib with *A. rhizogenes* ATCC 15834. Two to 3 weeks after inoculation hairy roots initiated at the inoculation site. The roots were then transferred to B5 medium with cefotaxime to eliminate agrobacteria. After several subcultures in this medium, the roots were transferred to antibiotic-free B5 medium. Confirmation of transformation with *A. rhizogenes* was done by PCR. These analyses showed that all the hairy roots harbored the rol genes. Liquid hairy root cultures were established in B5 medium and incubated under continuous dark at 28° C.

Figure 16:
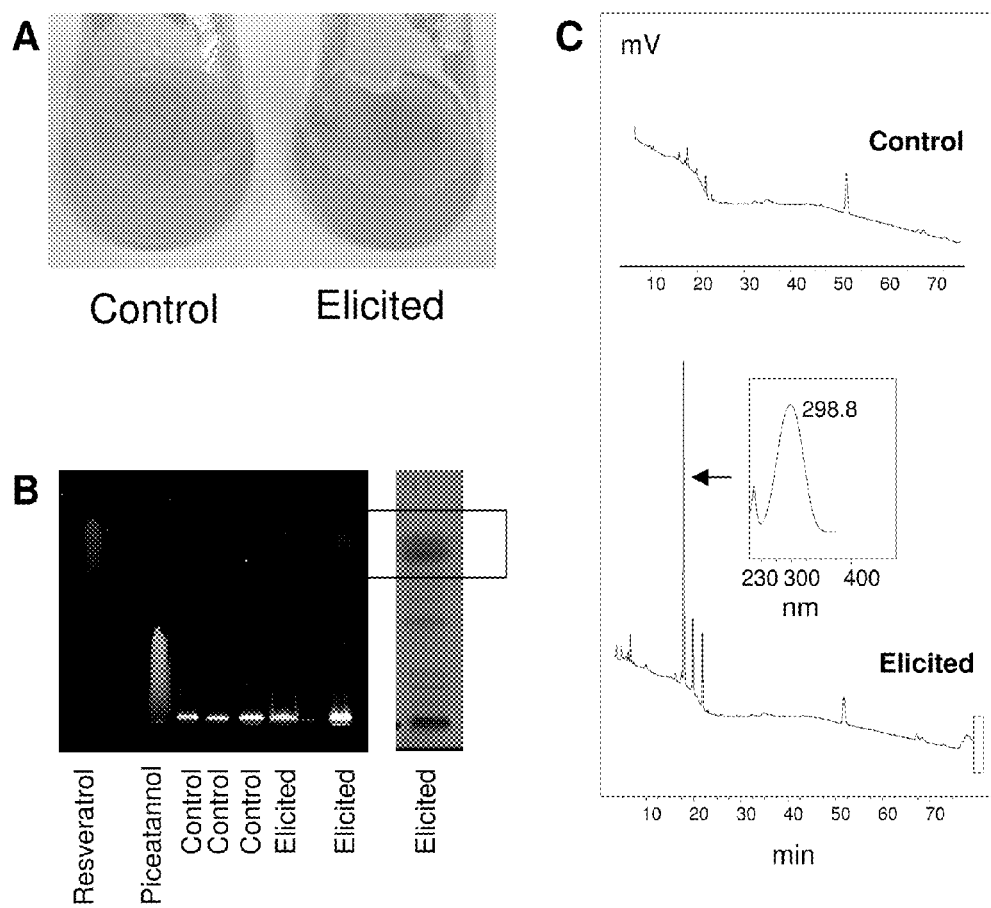
FIG. 16 shows elicitation of stilbenes in hairy roots of *Nicotiana benthamiana*. Hairy roots of *N. benthamiana*; B. HPTLC analyses showing inducible stilbenes (red box). C. HPLC chromatogram showing inducible stilbenes. Samples were separated on a SunFire C18 5 µm (4.6×250 mm) column using a Dionex P680 HPLC pump and mobile phase composed of acetonitrile and water with 0.5% formic acid. Stilbenes were detected with a coupled diode array and fluorescence (excitation 330 nm; emission 374 nm) detector. UV-spectrum of the major induced stilbene is shown in the insert.

To test for elicitation of stilbenes (pinosylvin, resveratrol and their derivatives), hairy root cultures of *N. benthamiana* lines 3NB, 4NB, 5NB and 6NB were grown for either 2 or 3 weeks as described above. Before elicitation the medium was removed and replaced with fresh B5 medium with 10.2 mM sodium acetate. Control cultures did not include sodium acetate. The medium was removed after 24 or 48 hours and compounds were extracted with ethyl acetate. HPTLC analyses showed that sodium acetate induced production and secretion of compounds with fluorescent characteristics of stilbene compounds (FIG. 16). In the figure HPTLC analyses shows inducible stilbenes (red box). The HPLC chromatogram shows inducible stilbenes. Samples were separated on a SunFire C18 5 μm (4.6×250 mm) column using a Dionex P680 HPLC pump and mobile phase composed of acetonitrile and water with 0.1% formic acid. Stilbenes were detected with a coupled diode away and fluorescence (excitation 330 nm; emission 374 nm) detector. UV-spectrum of the major induced stilbene is shown in the insert.

Further analyses were conducted by reverse phase HPLC. Extracts were separated on a SunFire C18 5 μm (4.6×250 mm) column using a Dionex P680 HPLC pump and a mobile phase composed of acetonitrile, water and formic acid. Stilbenes were detected with coupled diode array and fluorescence (excitation 330 nm; emission 374 nm) detectors. Analyses at 24 and 48 hours after elicitation showed that sodium acetate induced production of a major fluorescence compound with UV-spectrum of a putative pinosylvin or pinosylvin derivative compound. The amount of these compounds increased from 24 to 48 hours after elicitation. These compounds were further analyzed by HPLC-ESI-mass spectrometry. These analyses showed the presence of a putative pinosylvin derivative with a mass of m/z of 240.

Further confirmation of the pinosylvin structure is carried out. A synthetic pinosylvin derivative is used as a standard, and alternatively, may be purified from the hairy root medium with nuclear magnetic resonance analysis.

Example 7

Producing Stilbenes in Nicotiana tabacum

The methods of Example 6 are repeated, using Nicotiana tabacum and stilbene production measured.

Example 8

Producing Stilbenes in Polygonum cuspidatum

The methods of Example 6 are repeated, using rhizomes of Polygonum cuspidatum collected from the field and transferred to pots. New shoots that developed from the rhizomes are harvested and surface sterilized and cultured in liquid medium. Axenic shoots provide explants for A. rhizogenes inoculations and hairy root cultures are developed. Stilbene production is elicited and measured.

Example 9

Increasing Plant Biomass with a Plant Propagation System

Laboratory recovery of stilbenes. In the interest of scaling the production capacity of this hairy root system for high quality, natural resveratrol production and comparing different bioreactor platforms, an effective, universally-applicable quantitative method for resveratrol recovery is useful. Therefore we have calculated resveratrol recoveries based on the dry weight (DW) of the ethyl acetate extract of the culture media. The labscale recovery for trans-resveratrol ranged from 50 to 98 µg/mg extract DW, reflecting an approximate 60-fold increase above the levels of resveratrol detected in the non-elicited culture extracts (Table 3).

TABLE 3

Quantitation of resveratrol in ethyl acetate extracts of the medium and root tissue of non-elicited or sodium acetate-elicited hairy root cultures of peanut, line 2. Amounts are given in ng per mg extract.

| | Medium | | Root tissue | |
|---|---|---|---|---|
| | trans-Resveratrol | cis-Resveratrol | trans-Resveratrol | cis-Resveratrol |
| | Elicited | | | |
| A | 97992 | 387 | 253 | 10 |
| B | 85282 | 399 | 1134 | ND |
| C | 50339 | 47 | — | — |
| | Non-elicited | | | |
| D | 1416 | 31 | 210 | ND |
| E | 1813 | 8 | 587 | 3 |
| F | 692 | 9 | — | — |

Each sample (A to F) corresponds to the extract of an individual culture. The value for each sample is the mean of two determinations. ND, not detected; —, not analyzed.

Although cis-resveratrol was detected in both non-elicited and elicited cultures, the levels in the elicited cultures were relatively low ranging from 47 to 399 ng/mg media extract to an average of 10 ng/mg root tissue extract. This preferential production of the trans-over the cis-isomer is quite significant, as trans-resveratrol is known to be more active and thus the desired form for a resveratrol product (Roupe et al., 2006).

Estimating that 6 mg of culture medium ethyl acetate extract (DW or dry weight of the ethyl acetate extract; the ethyl acetate fraction is dried and weighed) is obtained from a gram of root tissue DW, the current production rate of this system ranges between 300-588 µg of trans-resveratrol per gram DW of root tissue. The levels of trans-resveratrol remaining in the root tissue were only 0.2-1.1 µg/mg extract DW (Table 2), suggesting that approximately 99% of the total trans-resveratrol produced in hairy roots is effectively secreted into the culture medium with sodium acetate elicitation.

Bioreactor production of stilbenes. A plant propagation apparatus, here a bioreactor, is used to increase plant biomass. An example of one such bioreactor is described at Adelberg et al., U.S. Pat. No. 6,753,178 ("Intermittent immersion vessel apparatus and process for plant propagation")

This bioreactor is a vessel adapted for receiving sterile growth media, the vessel having a length provided by a pair of opposing straight edge walls, the vessel further adapted to completely enclose plant tissue therein; a translucent platform for supporting the vessel, the platform responsive to a pivot which engages said platform, the platform pivoting in response to a motor operatively coupled thereto; wherein, as the platform pivots in response to the motor, the growth media within the vessel travels in a wave between opposite sides of the vessel and along the edge walls; and wherein the system further includes a linkage arm operatively connected at a first end to the platform, the linkage arm further operatively engaging along a second end a motor-driven cam. Here the bioreactor is used to increase hairy root culture biomass and production of resveratrol. The Liquid Lab™ rocker reactor from Southern Sun Biosystems, Inc. is used to grow hairy root cultures. The medium is exchanged every two weeks and pH and conductivity measurements will be recorded. To minimize chances of contamination, the biocide PPM™ (plant preservation mixtures) can be added at a concentration of about 0.02% after the first two weeks of culture. Peanut cultures are elicited after two weeks, and then repetitive elicited. Medium is collected after elicitation and resveratrol is recovered. Fresh medium is added and the elicitation process is repeated.

REFERENCES

Aggarwal, B. B., Bhardwaj, A., Aggarwal, R. S., Seeram, N. P., Shishodia, S., and Takada, Y. (2004) Role of Resveratrol in Prevention and Therapy of Cancer: Preclinical and Clinical Studies. Anticancer Res. 24:1-60.

Babu S K, Kumar K V, Subbaraju G V (2005) Estimation of trans-resveratrol in herbal extracts and dosage forms by high-performance thin-layer chromatography. Chem Pharm Bull 53:691-693. DOI 10.1248/cpb.53.691

Baur J, Sinclair D A (2006) Therapeutic potential of resveratrol: the in vivo evidence. Nat Rev Drug Discov. 5:493-506

Becker J, Armstrong G O, van der Merwe M J, Lambrechts M J, Vivier M A, Pretorius I S (2003) Metabolic engineering of Saccharomyces cerevisiae for the synthesis of the wine-related antioxidant resveratrol. FEMS Yeast Res 4:79-85.

Bru R, Selles S, Casado-Vela J, Belchi-Navarro S, Pedreno M A (2006) Modified cyclodextrins are chemically defined glucan inducers of defense responses in grapevine cell cultures. J Agri Food Chem. 54-65-71

Camilleri, C., Jouanin, L., 1991. The TR-DNA region carrying the auxin synthesis genes of the Agrobacterium rhizogenes agropine-type plasmid pRiA4: nucleotide sequence analysis and introduction into tobacco plants. Mol. Plant Microbe Interact. 4, 155-162.

Caspeta L, Quintero R, Villarreal M L (2005) Novel airlift reactor fitting for hairy root cultures: developmental and performance studies. Biotechnol Prog. 21:735-740

Celimene C, Micales J, Ferge L, Young R (1999) A. Efficacy of pinosylvins against white-rot and brown-rot fungi. Holzforschung. 53: 491-497

Chen R S, Wu P L, Chiou R Y (2002) Peanut roots as a source of resveratrol. J Agric Food Chem. 50:1665-1667

Chang, J-C., Lai, Y-H., Djoko, B., Wu, P.-L., Liu, C.-D., Liu, Y-W., and Chiou, R., Y-Y. (2006) Biosynthesis enhancement and antioxidant and anti-inflammatory activities of peanut arachidin-1, arachidin-3, and isopentadienylresveratrol. J. Agric. Food Chem. 54:10281-10287.

Chung I M, Park M R, Rehman S, Yun S J (2001) Tissue specific and inducible expression of resveratrol synthase gene in peanut plants. Mol Cells 12:353-359

Condori J, Medina-Bolivar F (2006) *Agrobacterium rhizogenes* strain ATCC 15834 plasmid pRi 15834 3-indoleacetamide hydrolase (aux2) and trytophan 2-monooxygenase (aux1) genes, complete cds. NCBI Accession No. DQ782955

Delmas D, Lancon A, Colin D, Jannin B, Latruffe N (2006) Resveratrol as a chemopreventive agent: a promising molecule for fighting cancer. Curr Drug Targets 7:423-442

Frankel E, Waterhouse A, Kinsella J (1993) Inhibition of human LDL oxidation by resveratrol. Lancet. 341:1103-1104.

Gamborg O L, Miller R A, Ojima K (1968) Nutrient requirements of suspension cultures of soybean root cells. Exp Cell Res 50:151-158

Gehm B D, McAndrews J M, Chien P Y, Jameson J L (1997) Resveratrol, a polyphenolic compound found in grapes and wine, is an agonist for the estrogen receptor. Proc Natl Acad Sci 94:14138-14143

Guillon S, Tremouillaux-Guiller J, Pati P K, Rideau M, Gantet P (2006) Hairy root research: recent scenario and exciting prospects. Curr Opi Plant Biol. 9:341-346

Hall D, De Luca V (2007) Mesocarp localization of a bifunctional resveratrol/hydroxycinnamic acid glucosyltransferase of Concord grape (*Vitis labrusca*). Plant J 49: 579-591.

Holsters M, de Waele D, Depicker A, Messens E, van Montagu M, Schell J (1998) Transfection and transformation of *Agrobacterium tumefaciens*. Mol Gen Genet. 163-181-187.

Huang Y, Tsai W, Shen C, Chen C (2005) Resveratrol derivatives from the roots of *Vitis thunbergii*. J Nat Prod 68: 217-220

Jeandet P, Douillet-Breuil A C, Bessis R, Debord S, Sbaghi M, Adrian M. (2002) Phytoalexins from the Vitaceae: biosynthesis, phytoalexin gene expression in transgenic plants, antifungal activity, and metabolism. J. Agric. Food. Chem. 50:2731-41.

Komamytsky S, Gaume A, Garvey A, Borisjuk N, Raskin I (2004) A quick and efficient system for antibiotic-free expression of heterologous genes in tobacco roots. Plant Cell Rep. 22: 765-773

Kopp P (1998) Resveratrol, a phytoestrogen found in red wine. A possible explanation for the conundrum of the 'French paradox'? Eur J Endocrinol. 138:619-620

Larronde F, Richard T, Delaunay J C, Decendit A, Monti J P, Krisa S, Merillon J M (2005) New stilbenoid glucosides isolated from *Vitis vinifera* cell suspension cultures (cv. Cabernet Sauvignon). Planta Med 71:888-890. DOI 10.1055/s-2005-871294

Lee J, Jung E, Lim J, Lee J, Hur S, Kim S S, Lim S, Hyun C G, Kim Y S, Park D. (2006) Involvement of nuclear factor-kappaB in the inhibition of pro-inflammatory mediators by pinosylvin. Planta Med. 72:801-806.

Medina-Bolivar F, Wright R, Funk V, Sentz D, Barroso L, Wilkins T, Petri Jr. W, Cramer C (2003) A non-toxic lectin for antigen delivery of plant-based mucosal vaccines. Vaccine 21:997-1005

Medina-Bolivar F, Cramer C (2004) Production of recombinant proteins in hairy roots cultured in plastic sleeve bioreactors In: Balbas P, Lorence A (eds) Recombinant gene expression: Reviews and protocols. Humana Press, Totowa, pp 351-363

Mikstacka, R., Rimando, A. M., Szalaty, K., Stasik, K., and Baer-Dubowska, W. (2006) "Effect of natural analogues of trans-resveratrol on cytochromes P4501A2 and 2E1 catalytic activities". Xenobiotica, 36: 269-285.

Miura D, Miura Y, Yagasaki K (2003) Hypolipidemic action of dietary resveratrol, a phytoalexin in grapes and red wine, in hepatoma-bearing rats. Life Sciences 73:1393-1400. DOI 10.1016/S0024-3205(03)00469-7

Nepote V, Grosso N R, Guzman C A (2004) Radical scavenging activity of extracts of argentine peanut skins (*Arachis hypogaea*) in relation to its trans-resveratrol content. J Argent Chem Soc 92:41-49

Nopo-Olazabal L, Woffenden B, Reed D, Buswell S, Zhang C, Medina-Bolivar F. Differential expression of the "super-promoter" in leaves and hairy roots of tobacco. 2005 In Vitro Biology Meeting, Abstract P-2037

Orallo F (2006) Comparative studies of the antioxidant effects of cis- and trans-resveratrol. Curr Med Chem. 13:87-98

Park E J, Min H Y, Ahn Y H, Bae C M, Pyee J H, Lee S K. (2004) Synthesis and inhibitory effects of pinosylvin derivatives on prostaglandin E2 production in lipopolysaccharide-induced mouse macrophage cells. Bioorg Med Chem Lett. 14:5895-5898.

Pitta-Alvarez, S., Giulietti, A., 1999. Influence of chitosan, acetic acid and citric acid on growth and tropane alkaloid production in transformed roots of *Brugmansia candida* Effect of medium pH and growth phase. Plant Cell Tissue Org. Cult. 59, 31-38.

Ramakrishnan D, Curtis W R (2004) Trickle-bed root culture bioreactor design and scale-up: growth, fluid-dynamics, and oxygen mass transfer. Biotechnol. Bioeng. 88:248-260.

Rimando A M, Barney D L (2005) Resveratrol and naturally occurring analogues in *Vaccinium* species. Acta Horticulture Proceedings 6:137-143

Rimando A M, Nagmani R, Feller D R, Yokoyama W (2005) Pterostilbene, a new agonist for the peroxisome proliferator-activated receptor α-isoform, lowers plasma lipoproteins and cholesterol in hypercholesterolemic hamsters. J Agric Food Chem 53:3403-3407

Roupe, K., Remsberg, C., Yanez, J., Davies, N., 2006a. Pharmacometrics of stilbenes: seguing towards the clinic. Curr. Clin. Pharm. 1, 81-101.

Roupe, K., Yanez, J., Teng, X. W., and Davies, N., 2006b. Pharmacometrics of selected stilbenes: srhapontigenin, piceatannol, pinosylvin. J. Pharm. Pharmacol. 58, 1443-1450.

Rudolf J R, Resurreccion A V (2005) Elicitation of resveratrol in peanut kernels by application of abiotic stresses. J Agric Food Chem 53:10186-10192. DOI 10.1021/jf0506737

Savary B, Flores H (1994) Biosynthesis of defense-related proteins in transformed root cultures of *Trichosanthes kirilowii* Maxim. var *japonicum* (Kitam.). Plant Physiol 106: 1195-1204

Schmülling, T., Schell, J., Spena, A., 1988. Single genes from *Agrobacterium rhizogenes* influence plant development. EMBO J. 7, 2621-2629.

Slightom, J. L., Durand-Tardif, M., Jouanin, L., Tepfer, D., 1986. Nucleotide sequence analysis of TL-DNA of *Agrobacterium rhizogenes* agropine type plasmid. Identification of open reading frames. J. Biol. Chem. 261, 108-121.

Soleas G J, Angelini M, Grass L, Diamandis E P & Goldberg D M. (2001) Absorption of trans-resveratrol in rats. Methods Enzymol., 335:145.

Tabata Y, Takano K, Ito T, Iinuma M, Yoshimoto T, Miura H, Kitao Y, Ogawa S, Hori O. (2007) "Vaticanol B, a resveratrol tetramer, regulates endoplasmic reticulum (ER) stress and inflammation." Am J Physiol Cell Physiol. E-Published; doi: 10.1152/ajpcell.00095.2007

Tassoni A, Fornale S, Franceschetti M, Musiani F, Michael A J, Perry B, Bagni N (2005) Jasmonates and Na-orthovanadate promote resveratrol production in *Vitis vinifera* cv. Barbera cell cultures. New Phytologist 166:895-905. DOI 10.1111/j.1469-8137.2005.01383.x Watts K T, Lee P C, Schmidt-Dannert C (2006) Biosynthesis of plant-specific stilbene polyketides in metabolically engineered *Escherichia coli*. BMC Biotechnology 6:22. DOI 10.1186/1472-6750-6-22

Wenzel, E., and Somoza, V., (2005) Metabolism and bioavailability of trans-resveratrol. Mol. Nutr. Food Res. 49:472-481.

White, F. F et al., (1985) J. Bacteriol., vol. 164, p. 33.

Wink M, Alfermann A W, Franke R, Wetterauer B, Distl M, Windhovel J, Krohn O, Fuss E, Garden H, Mohagheghzadeh A, Wildi E, Ripplinger P (2005) Sustainable bioproduction of phytochemicals by plant in vitro cultures: anticancer agents. Plant Gen Res. 3:90-100

---

What is claimed is:

1. A method of increasing production of a stilbene derivative in a stilbene composition, the method comprising producing a hairy root culture from a plant cell, and contacting said root culture with a substance that elicits production of a stilbene composition from said root culture such that said composition comprises higher amounts of one or more stilbene derivatives than resveratrol.

2. The method of claim 1, wherein said plant cell is selected from the group consisting of peanut, grape, and *Polygonum*.

3. The method of claim 1, wherein said substance is sodium acetate.

4. The method of claim 3, wherein the substance is about 5 mM to about 21 mM sodium acetate.

5. The method of claim 3, wherein the substance is about 10 mM sodium acetate.

6. A method of producing the stilbene composition of claim 1 wherein the hairy root culture is produced by the method comprising: infecting a plant cell with *Agrobacterium* selected from the group consisting of *Agrobacterium rhizogenes* and *Agrobacterium tumefaciens* such that said plant cell comprises a rol gene and an aux gene.

7. The method of claim 1, wherein said stilbene derivative comprises a derivative selected from the group consisting of glycosylated, prenylated, methylated and hydroxylated modifications of a stilbene.

8. The method of claim 1, wherein said stilbene composition comprises stilbene selected from the group consisting of resveratrol, a derivative of resveratrol, piceid, arachidin, pterostilbene, viniferin, pinosylvin, a derivative of pinosylvin, and derivatives of said stilbenes.

9. The method of claim 1 wherein said plant cell is from a plant that has the capacity to produce said stilbene composition.

10. The method of claim 1, wherein said substance is selected from the group consisting of sodium acetate, copper sulfate, methyl jasmonate, cellulase and chitosan.

11. The method of claim 1 wherein said composition comprises increased amounts of trans-isomer of a stilbene than cis-isomer of a stilbene.

12. The method of claim 6, wherein said *Agrobacterium tumefaciens* comprises a vector, said vector comprising at least one rol gene.

13. The method of claim 12, wherein said *Agrobacterium tumefaciens* comprises a single transfer DNA comprising the at least one rol gene and at least one aux gene.

14. The method of claim 1, wherein production level of said stilbene composition is raised by increasing the production of said root cultures, comprising exposing the root cells to chemical or physical stimuli or genetic modification.

15. The method of claim 1 wherein production of said stilbene composition is scaled up to commercial levels by increasing production of root cultures in a bioreactor.

16. The method of claim 1, wherein said stilbene composition is isolated from said root culture.

17. The method of claim 16, wherein said root culture comprises root tissue, media of said root culture, or a combination of same.

18. The method of claim 1, wherein said stilbene derivative comprises a derivative selected from the group consisting of a resveratrol derivative, piceid, arachidin, pterostilbene, viniferin and a derivative of pinosylvin.

19. The method of claim 11, wherein said composition comprises at least two times as much higher amounts of trans-isomer of a stilbene than cis-isomer of a stilbene.

20. The method of claim 11, wherein said composition comprises at least 10 times as much higher amounts of trans-isomer of a stilbene than cis-isomer of a stilbene.

21. The method of claim 11, wherein said composition comprises at least 100 times higher amounts of trans-isomer of a stilbene than cis-isomer of a stilbene.

22. The method of claim 11, wherein said composition comprises at least 1000 time of trans-isomer of a stilbene than cis-isomer of a stilbene.

23. A method of increasing production of a stilbene derivative from a plant host, the method comprising producing a hairy root culture from a plant cell, and contacting said root culture with a substance that elicits production of a stilbene composition from said root culture such that said composition produced by said hairy root culture comprises higher amounts of stilbene derivative than resveratrol compared to a composition produced by a plant cell culture.

* * * * *